(12) United States Patent
Engel et al.

(10) Patent No.: US 9,891,084 B2
(45) Date of Patent: Feb. 13, 2018

(54) GRAPHENE-BASED MAGNETIC HALL SENSOR FOR FLUID FLOW ANALYSIS AT NANOSCALE LEVEL

(71) Applicant: International Business Machines Corporation, Armonk, NY (US)

(72) Inventors: Michael Engel, Ossininng, NY (US); Rodrigo Neumann Barros Ferreira, Rio de Janeiro (BR); Mathias Steiner, Rio de Janiero (BR)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 15/467,084

(22) Filed: Mar. 23, 2017

(65) Prior Publication Data

US 2017/0191857 A1   Jul. 6, 2017

Related U.S. Application Data

(62) Division of application No. 14/944,766, filed on Nov. 18, 2015, now Pat. No. 9,702,748.

(60) Provisional application No. 62/241,594, filed on Oct. 14, 2015.

(51) Int. Cl.

| G01F 1/708 | (2006.01) |
|---|---|
| H01L 43/04 | (2006.01) |
| H01L 43/06 | (2006.01) |
| H01L 43/10 | (2006.01) |
| G01R 33/07 | (2006.01) |

(52) U.S. Cl.
CPC ............ *G01F 1/7088* (2013.01); *H01L 43/04* (2013.01); *H01L 43/06* (2013.01); *H01L 43/10* (2013.01); *G01R 33/07* (2013.01)

(58) Field of Classification Search
CPC .......... G01F 1/70; G01N 15/10; G01R 33/07; G01R 33/54; H01L 43/06
See application file for complete search history.

(56) References Cited

U.S. PATENT DOCUMENTS

| 8,190,372 B2 * | 5/2012 | Kahlman ............... B82Y 25/00 |
|---|---|---|
| | | 702/19 |
| 8,283,912 B2 | 10/2012 | Nieuwenhuis et al. |
| 8,664,940 B2 | 3/2014 | Bratkovski et al. |

(Continued)

FOREIGN PATENT DOCUMENTS

| CN | 102891251 A | 1/2013 |
|---|---|---|
| EP | 2208531 A1 | 7/2010 |
| KR | 1020100138849 A | 12/2010 |

OTHER PUBLICATIONS

Osterberg, Frederik W., et al., "Bead Capture on Magnetic Sensors in a Microfluidic System", IEEE Sensors Journal, vol. 9, No. 6, Jun. 2009, pp. 682-688.

(Continued)

*Primary Examiner* — Jewel V Thompson
(74) *Attorney, Agent, or Firm* — Harrington & Smith; Louis J. Percello

(57) ABSTRACT

A method of detecting a particle comprises magnetizing a particle using an AC magnetic field; generating an AC voltage in a sensing device having a conductive substantially 2-dimensional lattice structure from the magnetized particle; superimposing a DC magnetic field on the generated AC voltage in the sensing device; and measuring an AC Hall voltage at the sensing device.

17 Claims, 19 Drawing Sheets

(56) References Cited

U.S. PATENT DOCUMENTS

| | | | |
|---|---|---|---|
| 2004/0207396 A1 | 10/2004 | Xiao | |
| 2005/0035757 A1* | 2/2005 | Prins | B82Y 25/00 324/204 |
| 2011/0014719 A1 | 1/2011 | Sijbers et al. | |
| 2014/0292318 A1 | 10/2014 | Wang et al. | |
| 2014/0295460 A1 | 10/2014 | Weissleder et al. | |
| 2014/0346579 A1* | 11/2014 | Franke | G01R 33/07 257/295 |
| 2014/0374702 A1 | 12/2014 | Chu et al. | |
| 2015/0102807 A1* | 4/2015 | Eckinger | G01R 33/072 324/251 |
| 2015/0219544 A1* | 8/2015 | Liu | G01N 15/1031 506/39 |

OTHER PUBLICATIONS

Besse, Pierre A., et al., "Detection of a single magnetic microbead using a miniaturized silicon Hall sensor", Appl. Phys. Lett. 80,4199, (2002), abstract, 2 pgs.

Di Michele, Lorenzo, et al., "Single particle detection: Phase control in submicron Hall sensors", Journal of Applied Physics 108, 103918 (2010), 5 pgs.

Di Michele, Lorenzo, et al., "Detection and susceptibility measurements of a single Dynal bead", Journal of Applied Physics 110,063916, 2011, 6 gs.

Li, G1, et al., "Spin valve sensors for ultrasensitive detection of superpparamagnetic nanoparticles for biological applications", Sens. Actuators A Phys., 126(1):98-106, abstract, 2006, 1 pg.

Manzin, A., et al., "Modelling and optimization of submicron Hall sensors for the detection of superparamagnetic beads", J. Appl. Phys. 111,07E513, http://dx.doi.org/10.1063/1.3678322; abstract, 2012, 3 pgs.

Mihajlovic, Goran, et al., "Magnetic characterization of a single superparamagnetic bead by phase-sensitive micro-Hall magnetornetry", Appl. Phys. Lett. 91,172518, http://dx.doi.org/10.1063/1.2802732; abstract, 2007, 2 pgs.

Mihajlovic, Goran, et al., "Submicrometer Hall Sensors for Superparamagnetic Nanoarticle Detection", IEEE, vol. 43, Issue 6, abstract, 2015, 2 pgs.

Shen, Weifeng, et al., "Detection of DNA labeled with magnetic nanoparticles using MgO-based magnetic tunnel junciton sensors", Journal of Applied Physics 103,07A306, 2008, 3 pgs.

Panchal, V., et al., "Small epitaxial graphene devices for magnetosensing applications", Journal of Applied Physics, (111), 7,07E509, http://dx.doi.org/10.1063/1.3677769; 2012, 4 pgs.

Panchal, V., et al., "Epitaxial Graphene Sensors for Detection of Small Magnetic Moments", IEEE, vol. 49, Issue 1, 2015, 2 pgs.

Shen, Weifeng, et al. "In Situ detection of single micron-sized magnetic beads using magnetic tunnel junction sensors", Applied Physics Letters 86,253901, 2005, 3 pgs.

Shen, Weifeng, et al., "Quantitative detection of DNA labeled with magnetic nanoparticles using arrays of MgO-based magnetic tunnel junction sensors", Appl. Phys. Lett. 93,033903; http://dx.doi.org/10.1063/1/2963970; abstract, 2008, 2 pgs.

List of IBM Patents and Applications, 2 pgs.

* cited by examiner

GRAPHENE-BASED MAGNETIC HALL SENSOR FOR FLUID FLOW ANALYSIS AT NANOSCALE LEVEL

CROSS-REFERENCE TO A RELATED PATENT APPLICATION

This patent application is a divisional patent application of copending U.S. patent application Ser. No. 14/944,766, filed Nov. 18, 2015, which claims priority to U.S. Provisional Patent Application Ser. No. 62/241,594, filed Oct. 14, 2015, the disclosures of which are incorporated by reference herein in their entireties.

BACKGROUND

The exemplary embodiments of this invention relate generally to Hall-effect sensors and, more specifically, to graphene-based Hall-effect sensors and the use thereof for the characterization and analysis of fluid flow at micro-scale or nanoscale levels.

Velocimetry is the measurement of fluid velocity. Velocimetric techniques at microscale levels, such as Microscopic Particle Image Velocimetry (microPIV) and Microscopic Particle Tracking Velocimetry (microPTV), use optical (e.g., laser) detection and are, therefore, limited to microchannels etched in transparent materials, such as glass, polydimethylsiloxane (PDMS), and polymethyl methacrylate (PMMA). Both microPIV and microPTV techniques rely on the excitation of fluorescent microbeads using intense laser light pulses. Both techniques also have several limitations that prevent their application to fluid flow on a nanoscale level.

Magnetic nanoparticles can be used in various velocimetric techniques as markers for biological assays or tracers for fluid flow characterization. However, nanoparticles are generally on the order of about 1 nanometer (nm) to hundreds of nanometers in diameter. As such, their reduced size, weak magnetic field, large surface-to-volume ratio, and thermal disturbance (superparamagnetism) introduce challenges for achieving detectability in moving fluids.

The fabrication and integration of sensors and generators of magnetic fields into micro-/nanosystems designed to work with nanoparticles may be a complex and difficult task. Use of sensors and generators may also require advanced detection strategies to compensate for poor signal-to-noise ratio in the detection methods. Such detection strategies can be implemented within a CMOS-compatible process, but they can also be implemented in arbitrary substrate devices.

Previous attempts to detect small magnetic particles with Hall sensors employed Si—, InSb—, and graphene-based Hall devices and were able to detect the presence of magnetic microbeads composed of thousands of nanometer-sized iron oxide particles dispersed in a polymer matrix. However, the detection of moving nanoparticles was generally not possible, since the microbeads had to be positioned with highly complex apparatuses (atomic force microscopes (AFM), nanomanipulators, etc.) precisely on top of the sensors, since there was no integration of the sensors into micro-/nanofluidic channels. Furthermore, the sensor areas, which are typically about 1 square micrometer ($\mu m^2$) to about 6 $\mu m^2$, made it difficult or even impossible to integrate such sensors into certain micro-/nanofluidic devices. Aside from the difficulties associated with integrating the sensors into micro-/nanofluidic devices, the detection of single nanoparticles that are a few nanometers in diameter has not been demonstrated. Moreover, methods to characterize flow properties of a fluid through micro-/nanofluidic channels based on the exploration of dispersed magnetic nanoparticles have not been successfully carried out.

Alternatively, an $Al_2O_3$-based Magnetic Tunnel Junction (MTJ) has been used as a sensor for the detection of magnetic microbeads. The integration of this sensor into a microfluidic channel allowed for the detection of moving microbeads as they rolled on top of the MTJ. It was not, however, demonstrated how this approach could be used to detect the presence of single nanometer-sized magnetic particles, nor how the dispersed particles could be used to better characterize the flow of the surrounding fluid. Additionally, the relatively large size (about 10 $\mu m^2$) of the sensor hinders its integration into certain micro-/nanofluidic devices.

Along the same lines, MgO-based MTJs have been able to detect 2.5 micro molar ($\mu M$) target DNA labeled with 16 nm iron oxide nanoparticles. In doing so, the DNA strands were able to bond on the sensor surface. Provided the coverage was above a certain threshold, a signal was then detected denoting the presence of magnetic labels (nanoparticles). With this approach, it was not possible to detect single nanoparticles nor use them to characterize the flow of carrying fluid. It was also not possible to detect moving magnetic particles, since they had to be attached to the sensor surface for detection. Finally, the setup required a large array ($4 \times 10^4$ $\mu m^2$) of elliptical MTJ sensors, each one having a surface area of 85 $\mu m^2$, which made it unsuitable for integration into certain micro-/nanofluidic devices.

Micrometer- and submicrometer-sized Hall sensors using graphene, InSb, and InAs/AlSb (2-dimensional electron gas) have also been characterized and optimized with regard to the detection of very small magnetic fields. The ability to detect a few magnetic nanoparticles with such devices has not been demonstrated. In fact, these attempts did not even anticipate the detection of a single nanoparticle. Furthermore, assumptions made to carry out such attempts were based on a perfect placement of nanoparticles on top of the sensor and did not provide a method to detect moving nanoparticles, nor to determine the flow properties of the carrying fluid.

Another attempt at single-nanoparticle detection employed giant magnetoresistance (GMR) spin valve sensors to detect a few tens to hundreds of 16 nm iron oxide nanoparticles. However, in such attempts it was not possible to detect a single nanoparticle of comparable size. The detection method required the nanoparticles to be bound to the sensor and, therefore, did not provide a way to characterize the flow of the surrounding fluid.

Submicrometric semiconductor-based Hall sensors have also been shown to perform single-nanoparticle detection in the case of 50-175 nm nanoparticles made of thousands of smaller (4 nm) FePt nanoparticles. The compound nanoparticle was positioned by an intricate operation that required the presence of a Si membrane, which ultimately limited the sensitivity of the device. The method was not suitable for detecting moving nanoparticles nor for characterizing the surrounding fluid via the magnetic tracers. The detection of a single nanoparticle of only a few nanometers (<50 nm) with such devices was not demonstrated.

BRIEF SUMMARY

In one exemplary aspect, a method of detecting a particle comprises magnetizing a particle using an AC magnetic field; generating an AC voltage, from the magnetized particle, in a sensing device having a conductive substantially 2-dimensional lattice structure; superimposing a DC magnetic field on the generated AC voltage in the sensing device; and measuring an AC Hall voltage at the sensing device.

In another exemplary aspect, a method of determining a flow velocity field comprises magnetizing a particle in a fluid flowing in a channel by applying an AC magnetic field to the particle; measuring a first AC Hall voltage at a first sensing device in the channel, the first sensing device comprising a first graphene element biased with a voltage; measuring a second AC Hall voltage at a second sensing device in the channel, the second sensing device comprising a second graphene element biased with a voltage; determining a time-shift between the first measured AC Hall voltage and the second measured AC Hall voltage; and determining a fluid flow velocity in the channel based on the determined time-shift and a spatial distance between the first sensing device and the second sensing device.

In another exemplary aspect, an apparatus comprises a first coil for providing a DC magnetic field; a second coil for providing, an AC magnetic field; and a conductive substantially 2-dimensional lattice structure proximate the first coil and the second coil and being biased with a voltage. The first coil, the second coil, and the conductive substantially 2-dimensional lattice structure are separated by dielectric layers.

BRIEF DESCRIPTION OF THE SEVERAL VIEWS OF THE DRAWINGS

The foregoing and other aspects of exemplary embodiments are made more evident in the following Detailed Description, when read in conjunction with the attached Drawing Figures, wherein:

FIGS. 2A and 2B are schematic representations of side and top views, respectively, of a wafer defined by a substrate and a first dielectric layer, the wafer forming a portion of the sensor of. FIGS. 1A and 1B;

DETAILED DESCRIPTION

The exemplary embodiments described herein are directed to the detection and characterization of one or more magnetic nanoparticles, of about one to hundreds of nanometers in diameter, that operate as magnetic tracers, while dispersed in a carrying fluid that flows through a micro-/nanochannel. The exemplary embodiments are not limited to the detection and characterization of nanoparticles, however, as microparticles (particles that are-about one micrometer or larger in diameter) may also be detected. The apparatuses and methods used with the exemplary embodiments described herein allow for the characterization of the carrying fluid itself through information extracted from the magnetic tracers.

In embodiments of detecting and characterizing the magnetic nanoparticles, a conductive substantially 2-dimensional lattice structure (e.g., a graphene layer or sheet) of micro-/nanoscopic dimensions is integrated into a micro-/nanochannel and is biased with a voltage in order to promote the flow of a current. A nearby magnetic nanoparticle, flowing inside the micro-/nanochannel in a carrying fluid, is excited by an external magnetic field and creates a magnetic field at the graphene sheet. Due to the Hall effect, a detectable transversal Hall voltage is generated at the graphene sheet. The Hall voltage signal conveys information about the nearby magnetic nanoparticle and the flow properties of the carrying fluid. This allows for the detection of single nanoparticles with diameters from about 1 nanometer to hundreds of nanometers (as well as larger microparticles) while dispersed in a flowing fluid and for the use of this information to determine the fluid flow speed in micro-and nanochannels. Thus, the apparatuses and methods described herein facilitate techniques and processes associated with magnetic nanoparticle velocimetry.

Figure 1A:
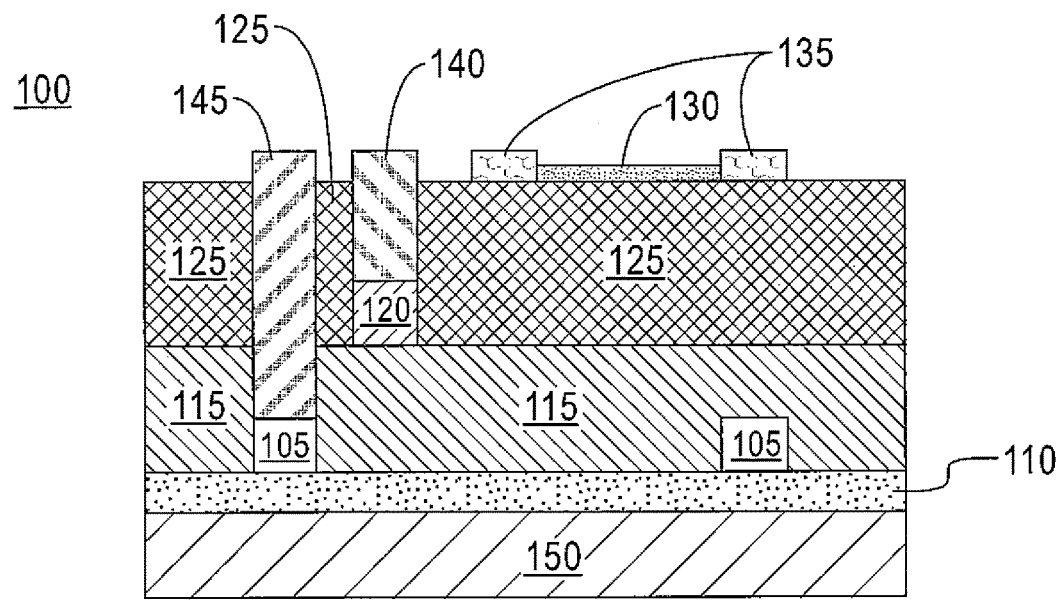
FIGS. 1A and 1B are schematic representations of side and top views, respectively, of one exemplary embodiment of a graphene-based Hall effect sensor.
Figure 1B:
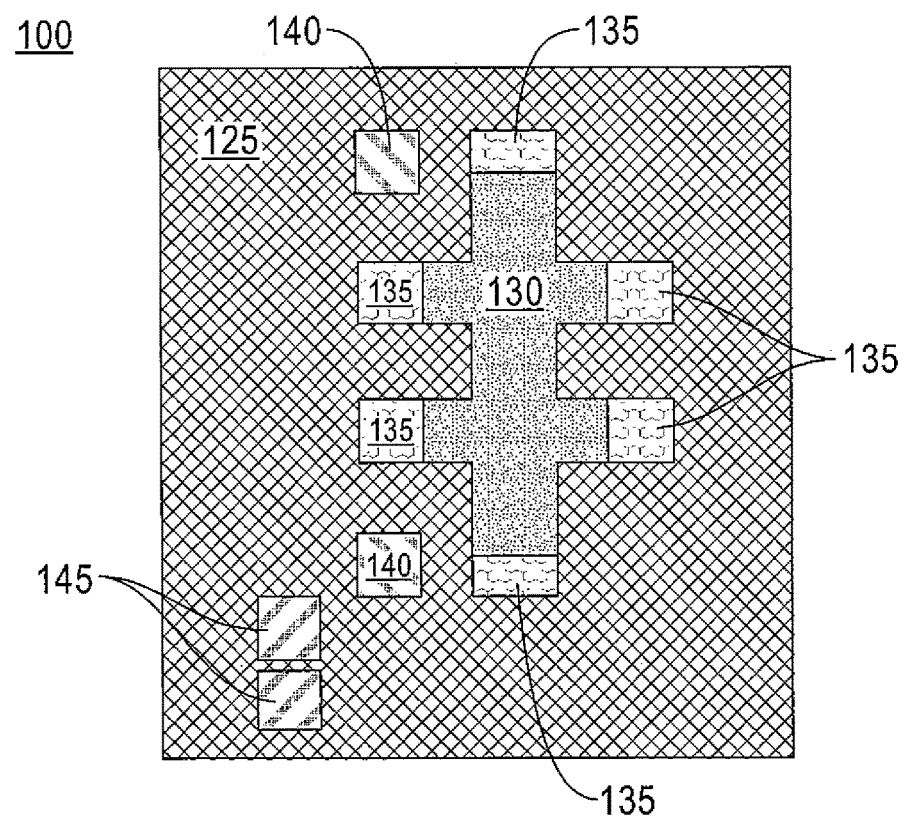

Referring to FIGS. 1A and 1B, a graphene-based magnetic Hall effect sensor is designated generally by the reference number 100 and is hereinafter referred to as "sensor 100." Sensor 100 comprises a first on-chip coil 105 disposed on a first dielectric layer 110 and covered by a second dielectric layer 115, a second on-chip coil 120 disposed on the second dielectric layer 115 and covered by a third dielectric layer 125, a conductive substantially 2-dimensional lattice structure 130 disposed on the third dielectric layer 125, a first set of contacts 135 disposed on the third dielectric layer 125 and adjacent to the substantially 2-dimensional lattice structure 130, a first set of vias 145 formed through the third dielectric layer 125 and the second dielectric layer 115 to the first on-chip coil 105, and a second set of vias 140 formed through the third dielectric layer 125 to the second on-chip coil 120. The first dielectric layer 110 may be disposed on a solid or flexible substrate 150. The first on-chip coil 105 produces a direct current (DC) magnetic field. The second on-chip coil 120 produces an alternating current (AC) magnetic field.

The conductive substantially 2-dimensional lattice structure 130 may be any suitable single-layer or multi-layer organic or inorganic layered material such as graphene, $MoS_2$, $WSe_2$, black phosphorous, regular arrays or random networks/thin films made of quasi-one dimensional lattice structures such as organic and inorganic nanotubes/nanowires (e.g. carbon nanotubes, Si nanowires, etc.), combinations of any of the foregoing materials, or the like. However, the substantially 2-dimensional lattice structure 130 is hereinafter referred to as "graphene 130."

Referring now to FIGS. 2A through 14, examples of the main process steps by which the sensor 100 can be fabricated are shown and described.

Figure 2A:
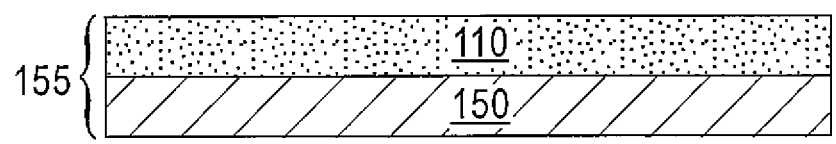
Figure 2B:
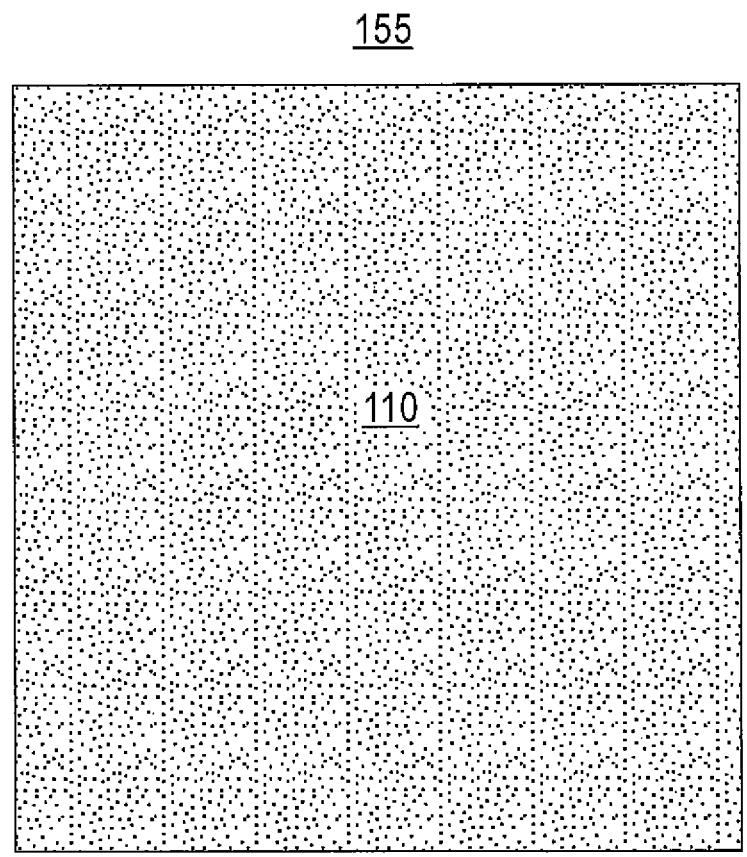

As shown in FIGS. 2A and 2B, the substrate 150 can be an insulating, planarized substrate coated by the first dielectric layer 110 to form a wafer 155. The substrate 150 may comprise, for example, one or more of glass, quartz, SiC, a silicon nitride such as $Si_3N_4$, plastic, and the like. Suitable dielectric materials for the first dielectric layer 110 include, but are not limited to, $SiO_2$, $Al_2O_3$, HfO, combinations of the foregoing, and the like. Such dielectric materials may be deposited via standard processes such as atomic layer deposition, thermal evaporation, or chemical vapor deposition (CVD).

Figure 3A:
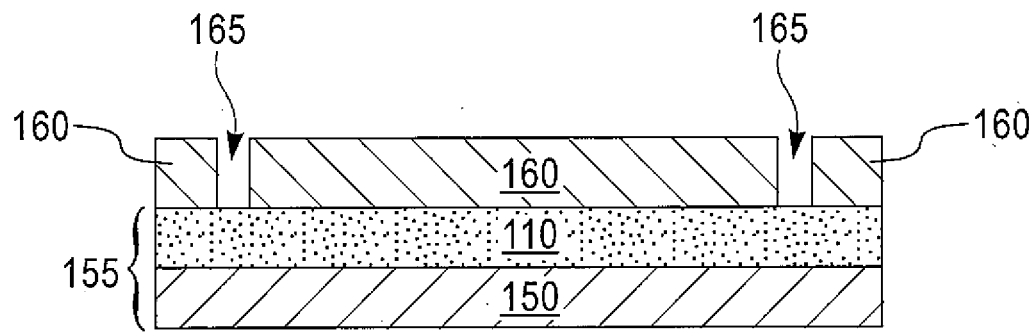
FIGS. 3A and 3B are schematic representations of side and top views, respectively, of a photo-resist material deposited onto the wafer and patterned.
Figure 3B:
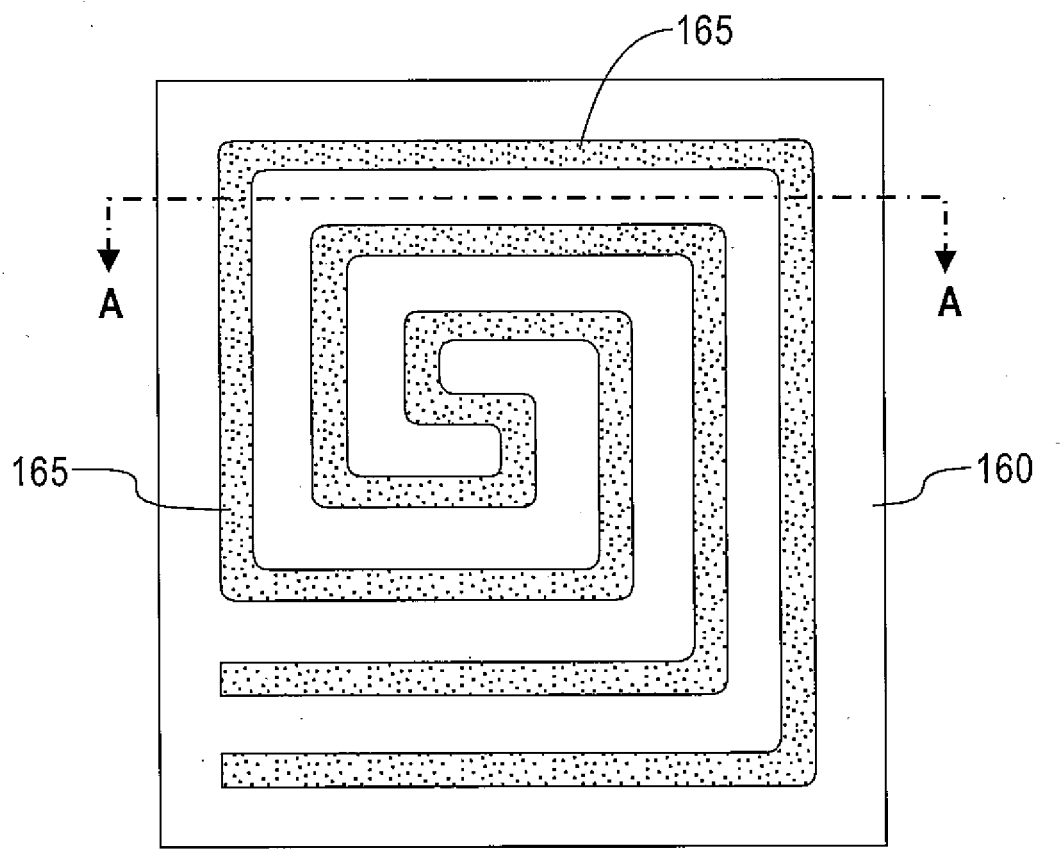

As shown in FIGS. 3A and 3B, the wafer 155 may be coated with a positive photo-resist material (e.g., PMMA) for production of a mask 160, followed by patterning using an e-beam or photolithography technique to expose portions of the photo-resist, and a develop step to remove exposed areas 165. Generally, the mask 160 can be a soft mask, like optical or electron-beam lithography resist (e.g. PMMA, hydrogen silsesquioxane (HSQ), or polysilicon-based material (such as MICROPOSIT S1818 from available suppliers)) or a hard mask, likean oxide, nitride, or metal deposited by a compatible deposition method.

Figure 4A:
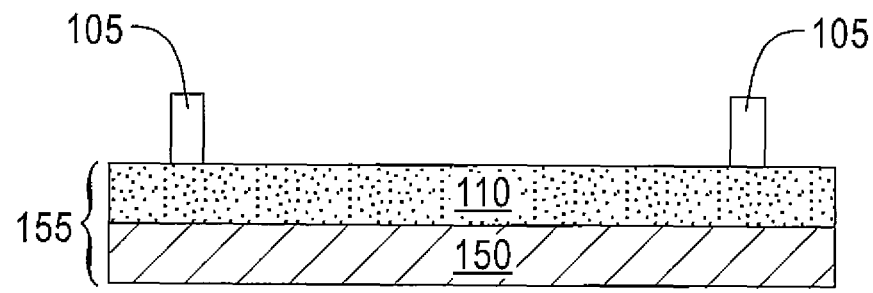
FIGS. 4A and 4B are schematic representations of side and top views, respectively, of a metallic thin film forming a first on-chip coil on the wafer.
Figure 4B:
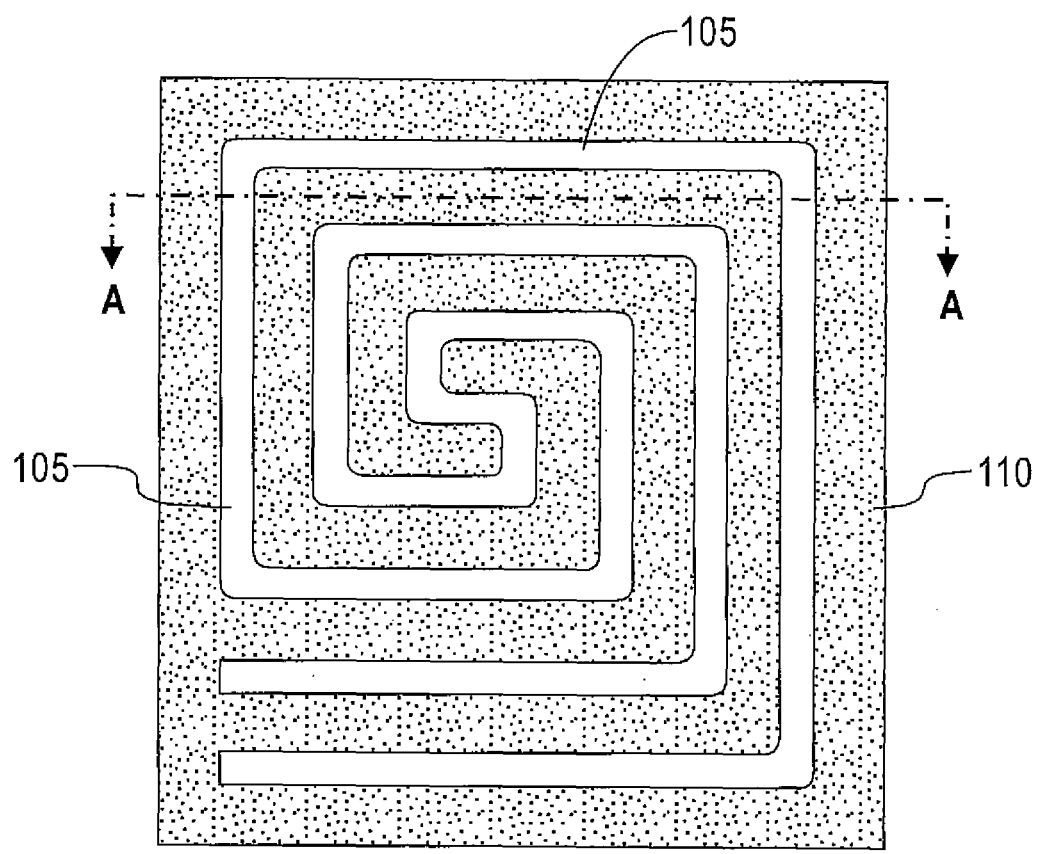

As shown in FIGS. 4A and 4B, a metallic thin film may be deposited in the removed portions of the exposed areas 165 and onto the first dielectric layer 110 by means of a standard metal deposition process. This metallic thin film will form the first on-chip coil 105 for producing the DC magnetic field. Suitable metals for the metallic thin film to form the first on-chip coil 105 include, but are not limited to, W, Ti, Pd, Au, Cr, and the like. The mask 160 can be removed using any suitable lift off technique.

Figure 5A:
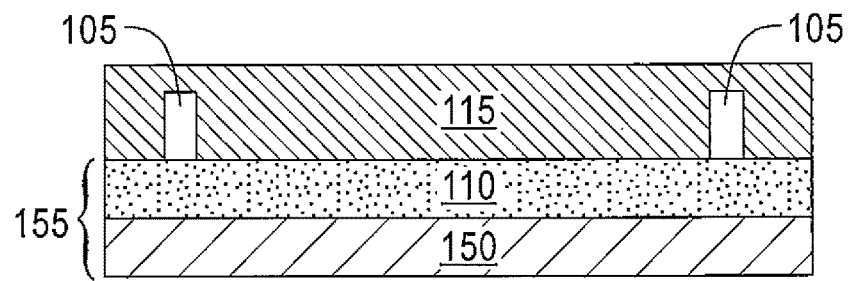
FIGS. 5A and 5B are schematic representations of side and top views, respectively, of a second dielectric layer deposited onto the first on-chip coil.
Figure 5B:
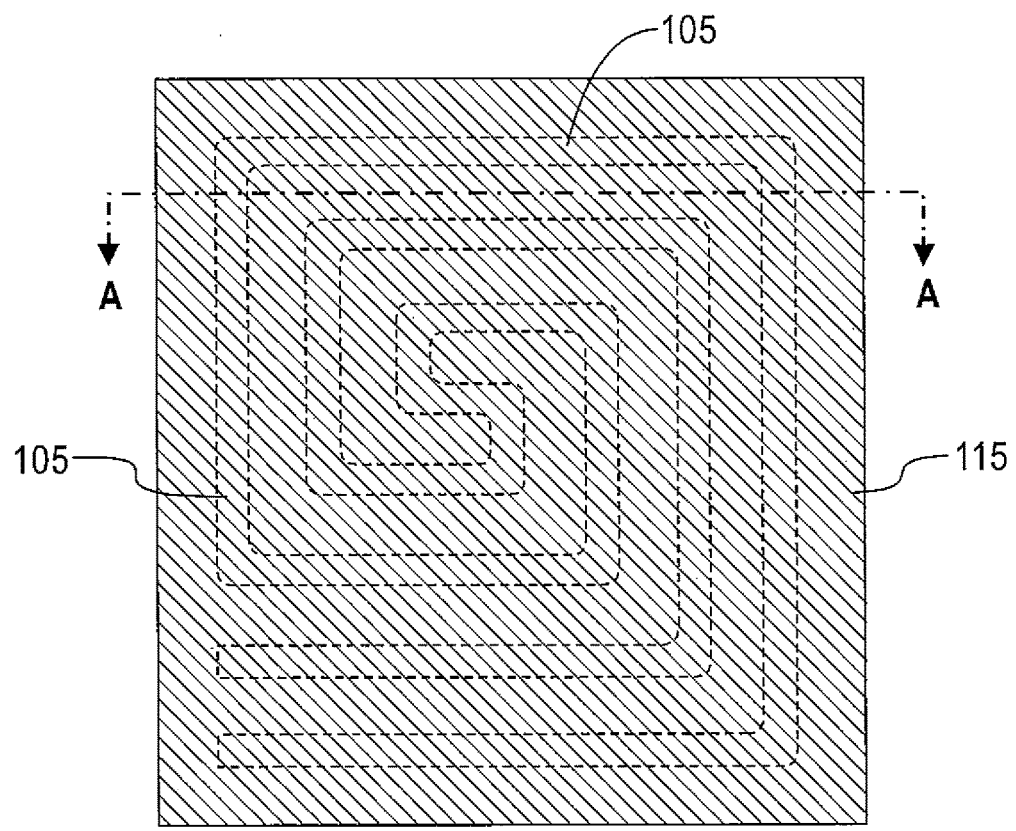

As shown in FIGS. 5A and 5B, the first on-chip coil 105 may be coated with the second dielectric layer 115 such that the metallic thin film defining the first on-chip coil 105 is completely covered. The second dielectric layer 115 may then be planarized. Suitable dielectrics for the second dielectric layer 115 include, but are not limited to, $SiO_2$, $Al_2O_3$, HfO, combinations of the foregoing, and the like, which may be deposited via standard processes such as atomic layer deposition, thermal evaporation, or CVD.

Figure 6A:
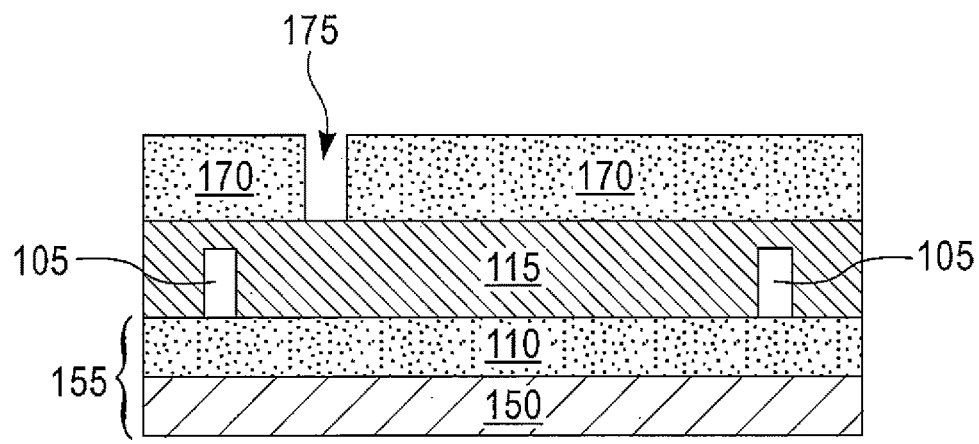
FIGS. 6A and 6B are schematic representations of side and top views, respectively, of a photo-resist material deposited onto the second dielectric layer, the photo-resist material being patterned.
Figure 6B:
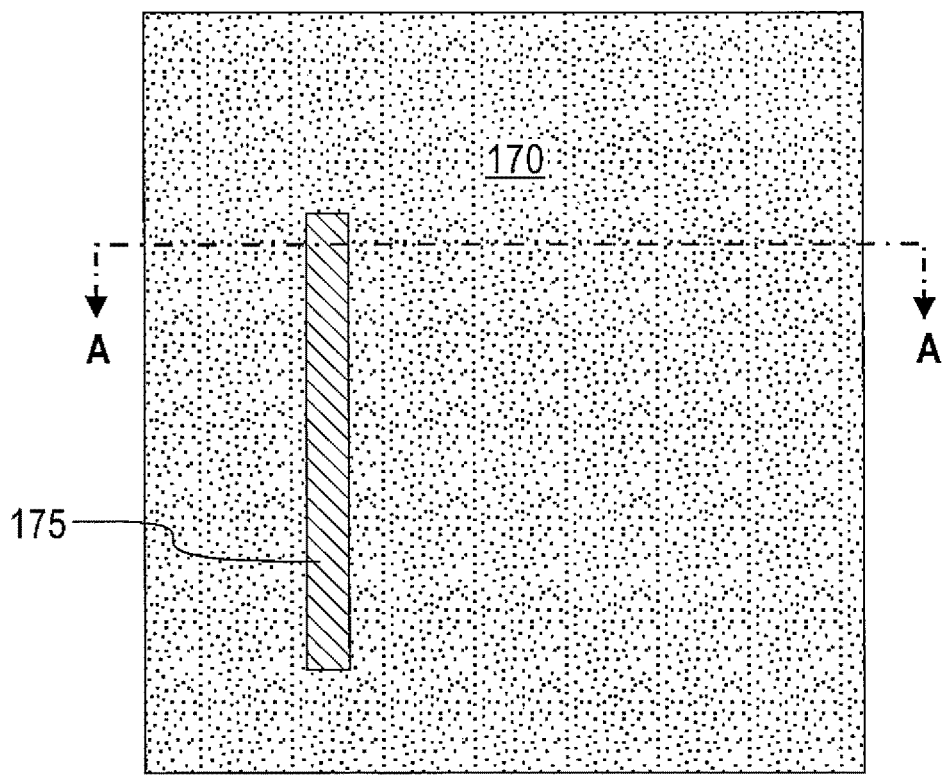

As shown in FIGS. 6A and 6B, the second dielectric layer 115 may be coated with a positive photo-resist (e.g., PMMA) to produce a second mask 170, followed by patterning using an e-beam or photolithography technique to expose portions of the photo-resist, and a develop step to remove exposed areas 175. Generally, the second mask 170 can be a soft mask, like optical or electron-beam lithography resist (e.g., PMMA, HSQ, or S1818) or a hard mask, like an oxide, nitride, or metal deposited by a compatible deposition method.

Figure 7A:
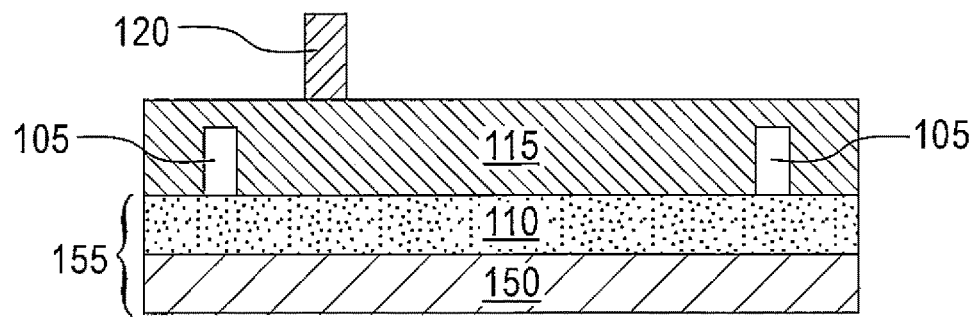
FIGS. 7A and 7B are schematic representations of side and top views, respectively, of a metallic thin film forming a second on-chip coil on the second dielectric layer.
Figure 7B:
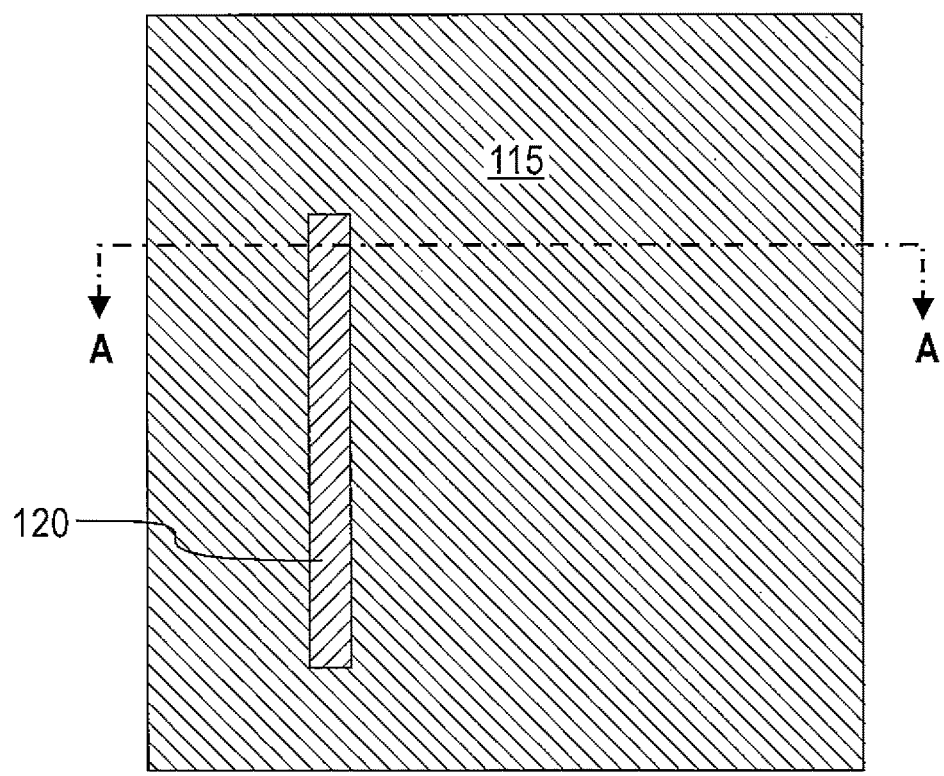

As shown in FIGS. 7A and 7B, a metallic thin film may be deposited in the removed portions of the exposed areas 175 and onto the second dielectric layer 115 by means of a standard metal deposition process. This metallic thin film forms the second on-chip coil 120 for producing the AC magnetic field. The second on-chip coil 120 may be a thin linear element, as shown in FIG. 7B. Suitable metals for the metallic thin film to form the second on-chip coil 120 include, but are not limited to, W, Ti, Pd, Au, Cr; and the like. The second mask 170 can be removed using any suitable lift off technique.

Figure 8A:
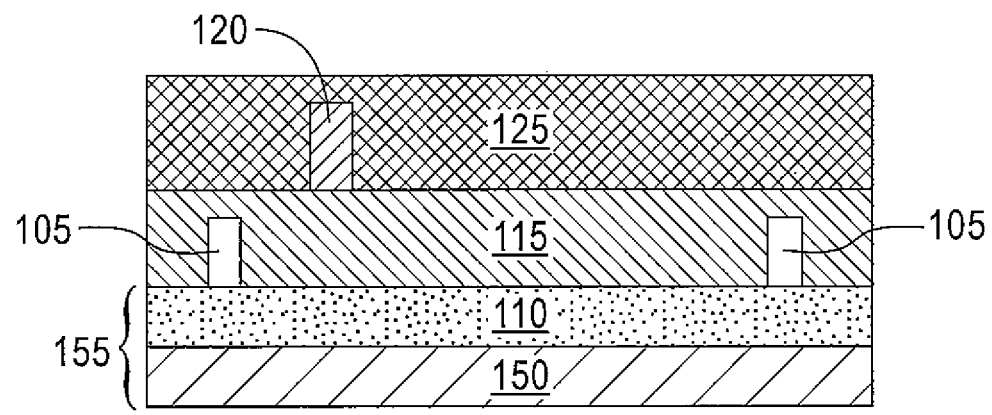
FIGS. 8A and 8B are schematic representations of side and top views, respectively, of a third dielectric layer deposited onto the second on-chip coil.
Figure 8B:
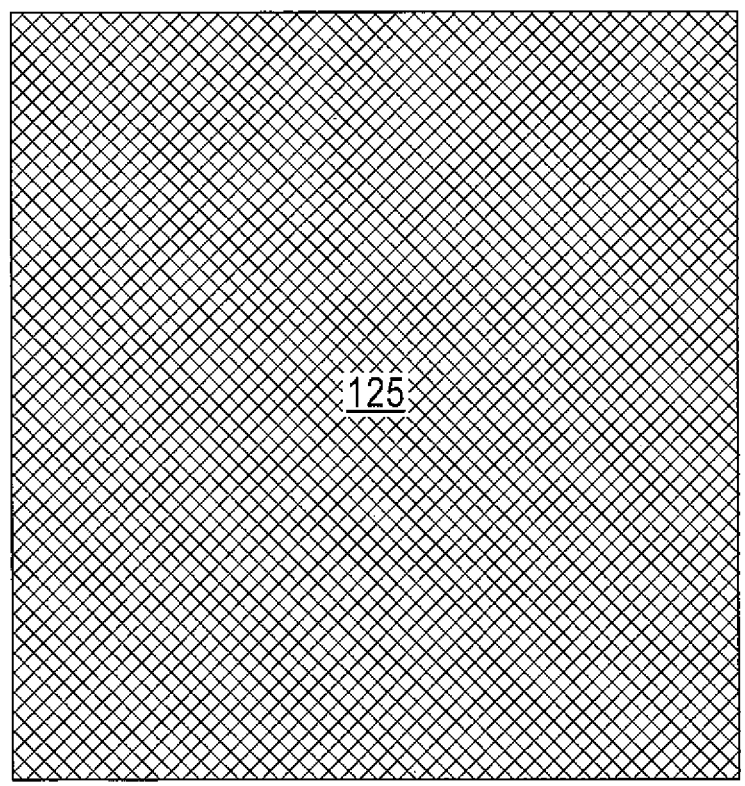

As shown in FIGS. 8A and 8B, the second on-chip coil 120 may be coated with the third dielectric layer 125 such that the metallic thin film defining the second on-chip coil 120 is completely covered. The third dielectric layer 125 may then be planarized. Suitable dielectrics for the third dielectric layer 125 include, but are not limited to, $SiO_2$, $Al_2O_3$, HfO, combinations of the foregoing, and the like, which may be deposited via standard processes such as atomic layer deposition, thermal evaporation, or CVD.

Figure 9A:
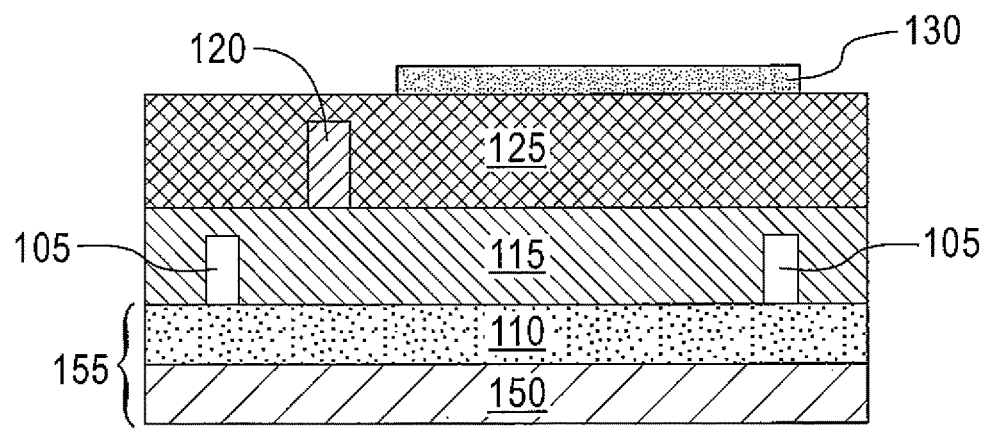
FIGS. 9A and 9B are schematic representations of side and top views, respectively, of a graphene layer deposited on the third dielectric layer.
Figure 9B:
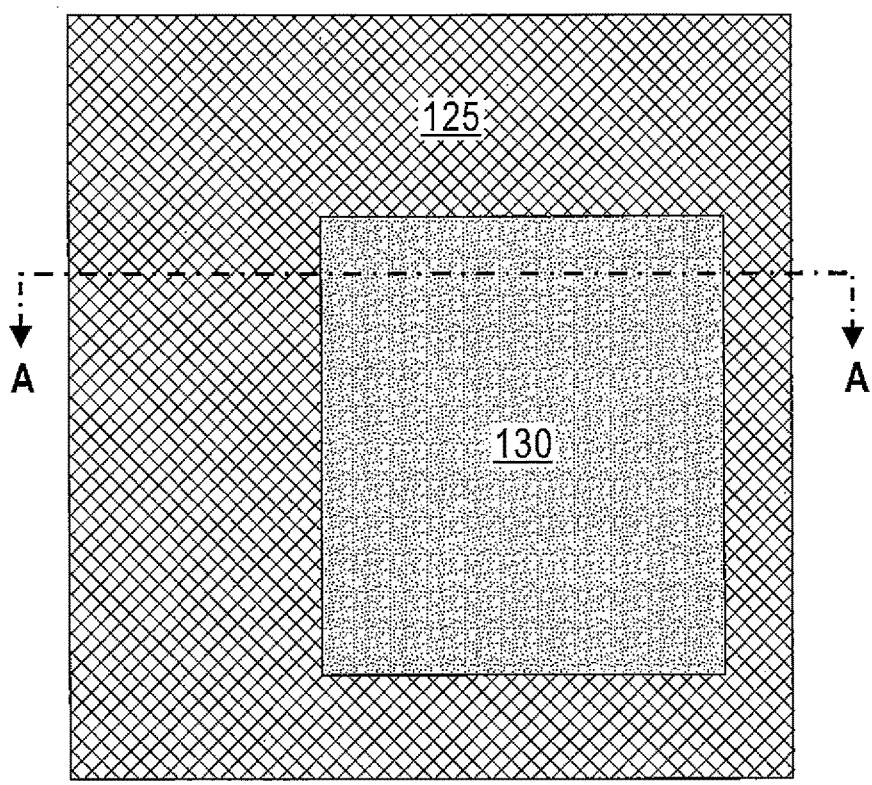

As shown in FIGS. 9A and 9B, graphene may be disposed onto the planarized top surface of the third dielectric layer 125 to provide the graphene 130 as a layer. One suitable method of depositing the graphene includes, but is not limited to, deposition of the graphene on a copper foil using CVD to synthesize the layer, followed by dissolving the copper such that the graphene floats on water, and subsequently transferring the floating graphene onto the planarized top surface of the third dielectric layer 125.

Figure 10A:
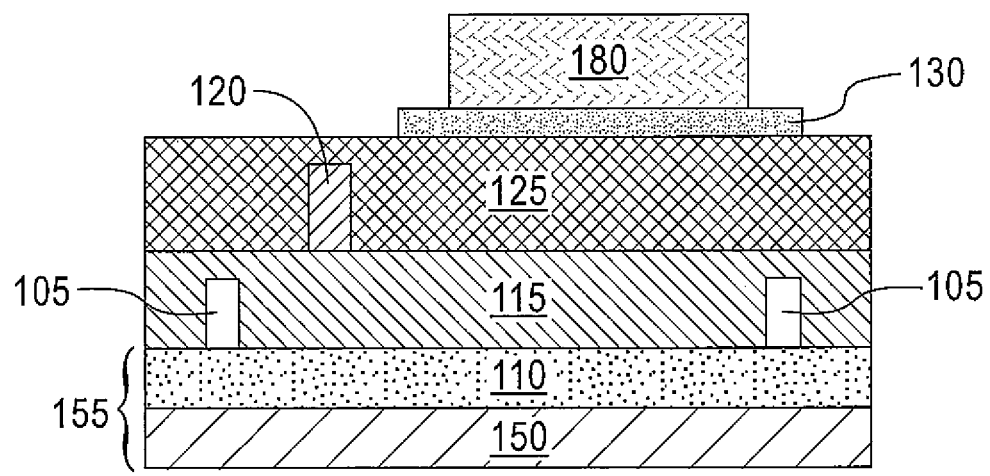
FIGS. 10A and 10B are schematic representations of side and top views, respectively, of a photo-resist material deposited onto the graphene layer, the photo-resist material being patterned.
Figure 10B:
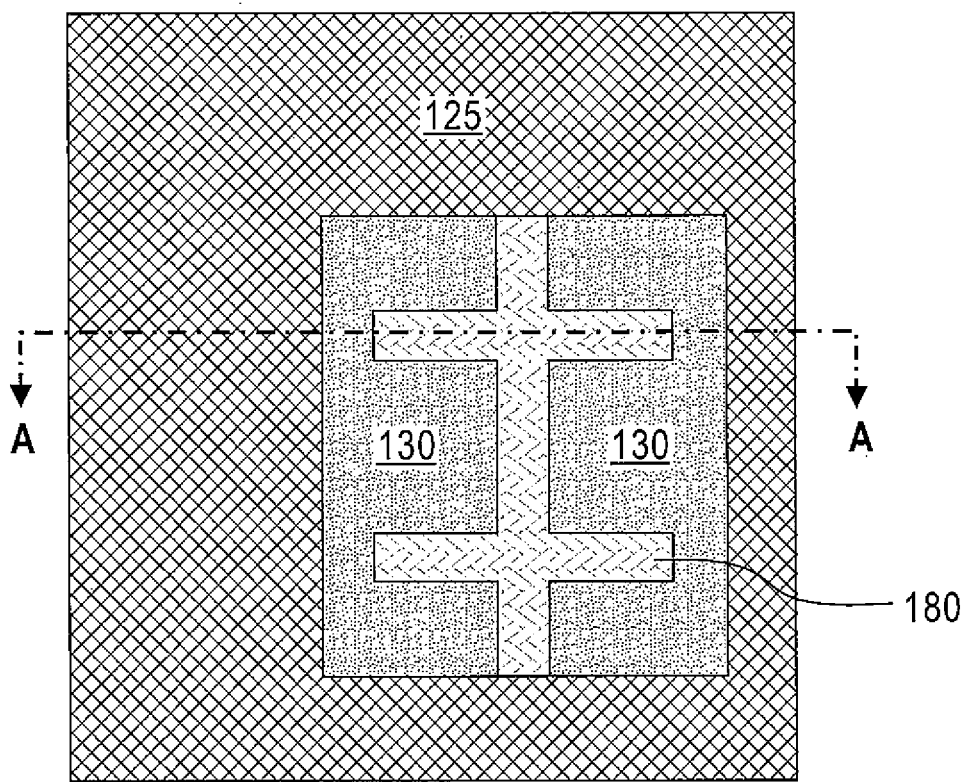

As shown in FIGS. 10A and 10B, the graphene 130 may then be coated with a negative photoresist (e.g, PMMA) to produce a third mask 180 followed by patterning using an e-beam or photolithography technique to expose portions of the negative photo-resist, and a develop step to remove non-exposed areas of the third mask 180. Generally, the third mask 180 can be a soft mask, like optical or electron-beam lithography resist (e.g., PMMA, HSQ, or S1818) or a hard mask, like an oxide, nitride, or metal deposited by a compatible deposition method.

Figure 11A:
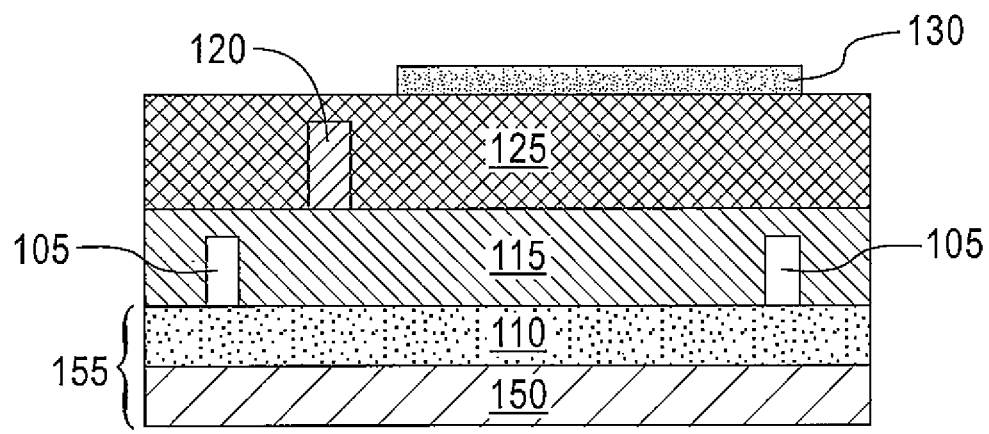
FIGS. 11A and 11B are schematic representations of side and top views, respectively, of the graphene layer after an etch process.
Figure 11B:
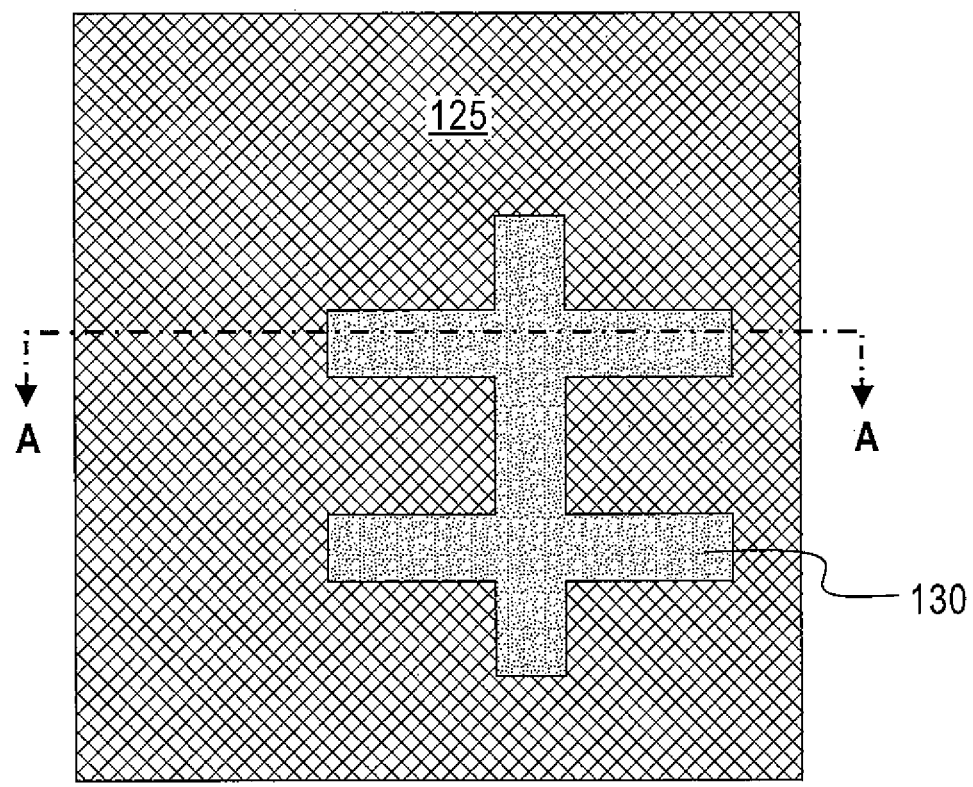

As shown in FIGS. 11A and 11B, the exposed portions of the graphene 130 (which were under the removed non-exposed. areas of the third mask 180) may be etched by a suitable technique (e.g., oxygen reactive ion etching (RIE)). This may leave the graphene 130 in a cross-type pattern on the third dielectric layer 125.

Figure 12A:
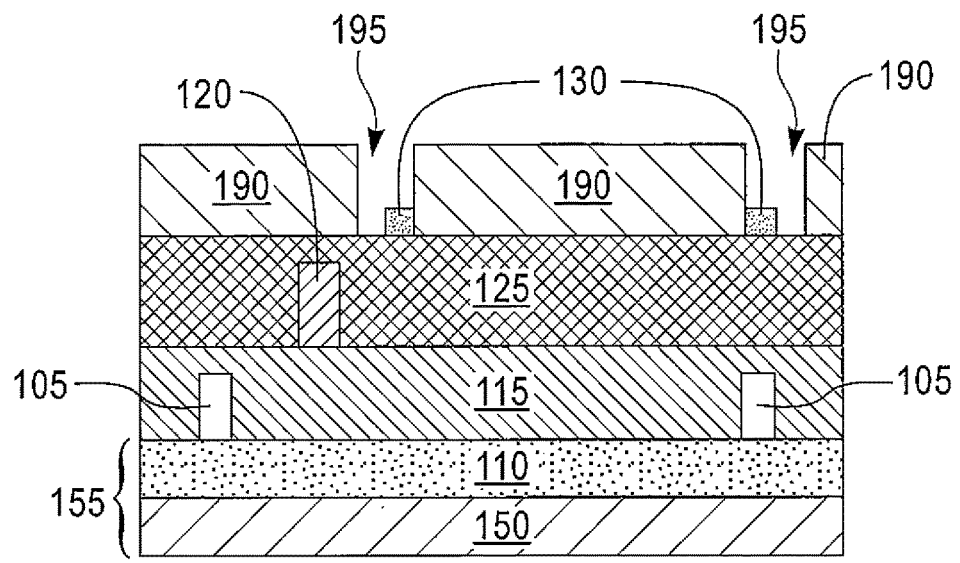
FIGS. 12A and 12B are schematic representations of side and top views, respectively, of a photo-resist material deposited onto the graphene and the third dielectric layer, the photo-resist material being patterned.
Figure 12B:
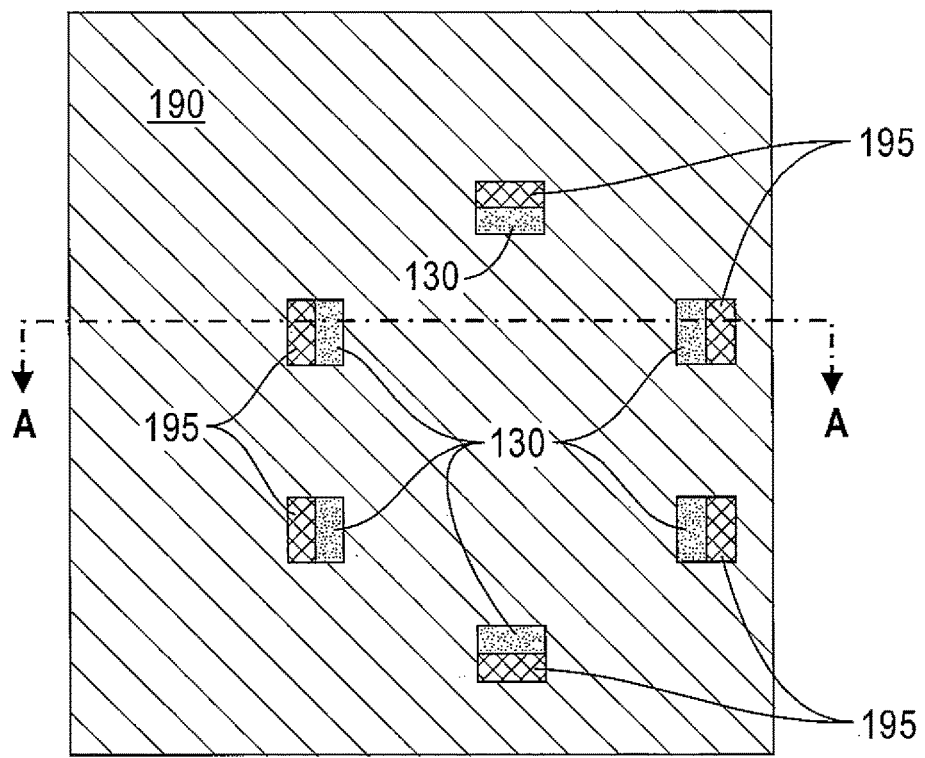

As shown in FIGS. 12A and 12B, the graphene 130 and the top surface of the third dielectric layer 125 may be coated with a positive photo-resist (e.g., PMMA) to produce a fourth mask 190 followed by patterning using an e-beam or photolithography technique to expose portions of the positive photo-resist, and a develop step to remove exposed areas 195 of the fourth mask 190. Generally, the fourth mask 190 can be a soft mask, like optical or electron-beam lithography resist (e.g., PMMA, HSQ, or S1818) or a hard mask, like an oxide, nitride, or metal deposited by a compatible deposition method.

Figure 13A:
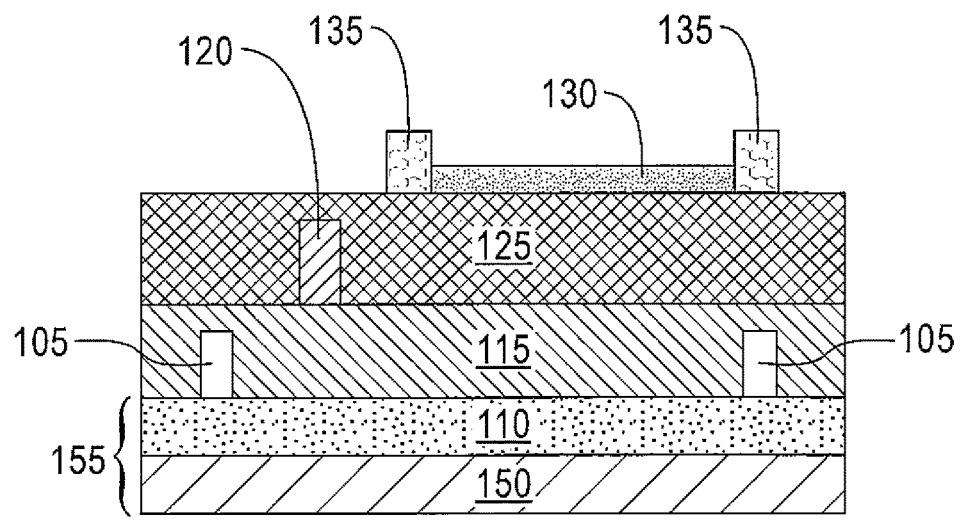
FIGS. 13A and 13B are schematic representations of side and top views, respectively, of a set of contacts formed adjacent the graphene.
Figure 13B:
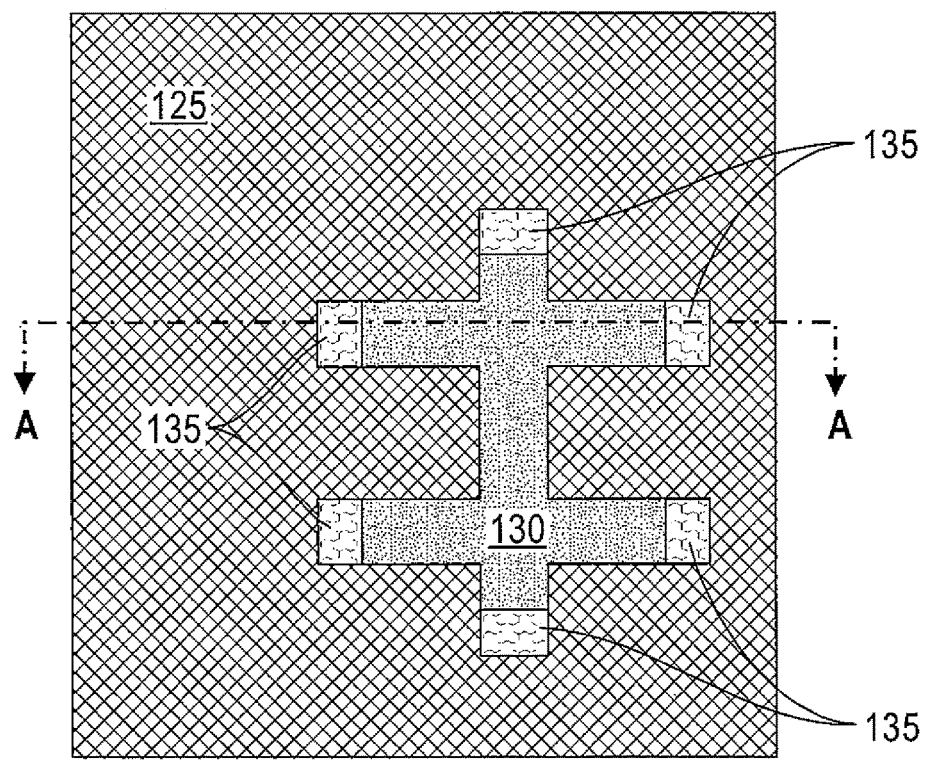

As shown in FIGS. 13A and 13B, a metallic thin film may be deposited in the removed exposed areas 195 and onto the third dielectric layer 125 adjacent to the graphene 130 by means of a standard metal deposition process. This third metal film deposited in the removed exposed areas 195 forms the first set of contacts 135. Suitable metals for the third metal film to form the first set of contacts 135 include, but are not limited to, W, Ti, Pd, Au, Cr, and the like.

Figure 14:
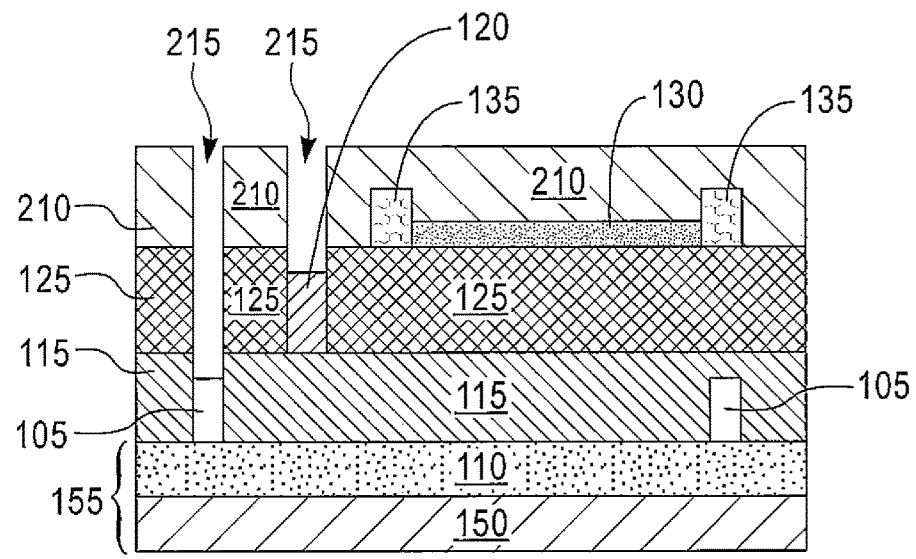
FIG. 14 is a schematic representation of a side view of a photo-resist material deposited over the graphene and the set of contacts, the photo-resist material being patterned.

As shown in FIG. 14, the top surface of the third dielectric layer 125, the graphene 130, and the first set of contacts 135 may be coated with a positive photo-resist (e.g., PMMA) to produce a fifth mask 210 followed by patterning using an e-beam or photolithography technique to expose portions of the positive photo-resist, and a develop step to remove exposed areas 215 of the fifth mask 210. Generally, the fifth mask 210 can be a soft mask, like optical or electron-beam lithography resist (e.g., PMMA, HSQ, or S1818) or a hard mask, like an oxide, nitride, or metal deposited by a compatible deposition method.

Open areas under the exposed areas 215 of the fifth mask 210 can be sequentially etched using any suitable etching method (such as RIE) to open areas of the third dielectric layer 125 down to the second on-chip coil 120 and to open areas of the third dielectric layer 125 and the second dielectric layer 115 down to the first on-chip coil 105.

Referring back to FIGS. 1A and 1B, the opened areas down to the second on-chip coil 120 and down to the first on-chip coil 105 may be followed with deposition of a metallic thin film into the opened areas by means of a standard metal deposition process. This deposition of metal forms the first set of vias 145 through the third dielectric layer 125 and the second dielectric layer 115 to the first on-chip coil 105 and the second set of vias 140 through the third dielectric layer 125 to the second on-chip coil 120.

Figure 15:
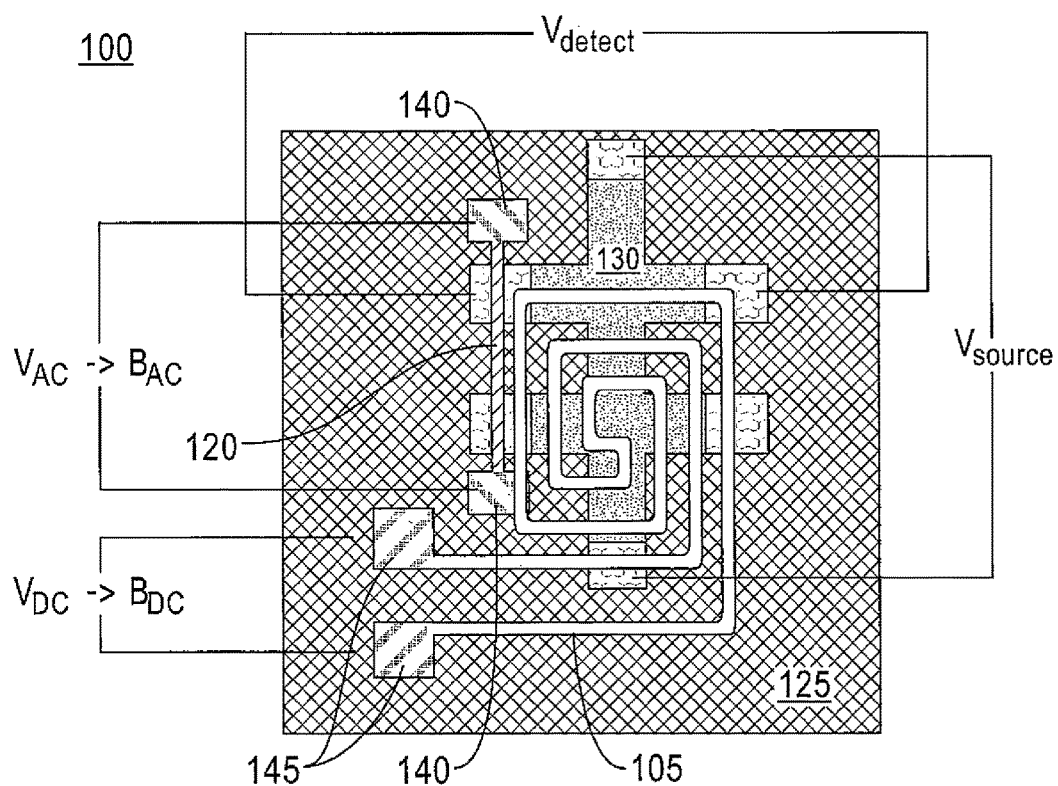
FIG. 15 is a schematic representation of a top view of an overlay of a first on-chip coil, a second on-chip coil, and a graphene layer of the graphene-based Hall effect sensor and showing various voltages.

Referring now to FIG. 15, the overlay of the different metal layers (forming the first on-chip coil 105 and the second on-chip coil 120) and the graphene 130 is schematically shown. Source voltage ($V_{source}$) is shown across opposing ends of the graphene 130. Other measured voltages are also indicated. For example, a measured voltage across the graphene 130 in the direction of flow when the sensor 100 is located in a fluid is indicated at $V_{detect}$. The AC and DC voltages are also indicated as $V_{AC}$ and $V_{DC}$ across the first set of vias 140 and the second set of vias 145, respectively.

Figure 16:
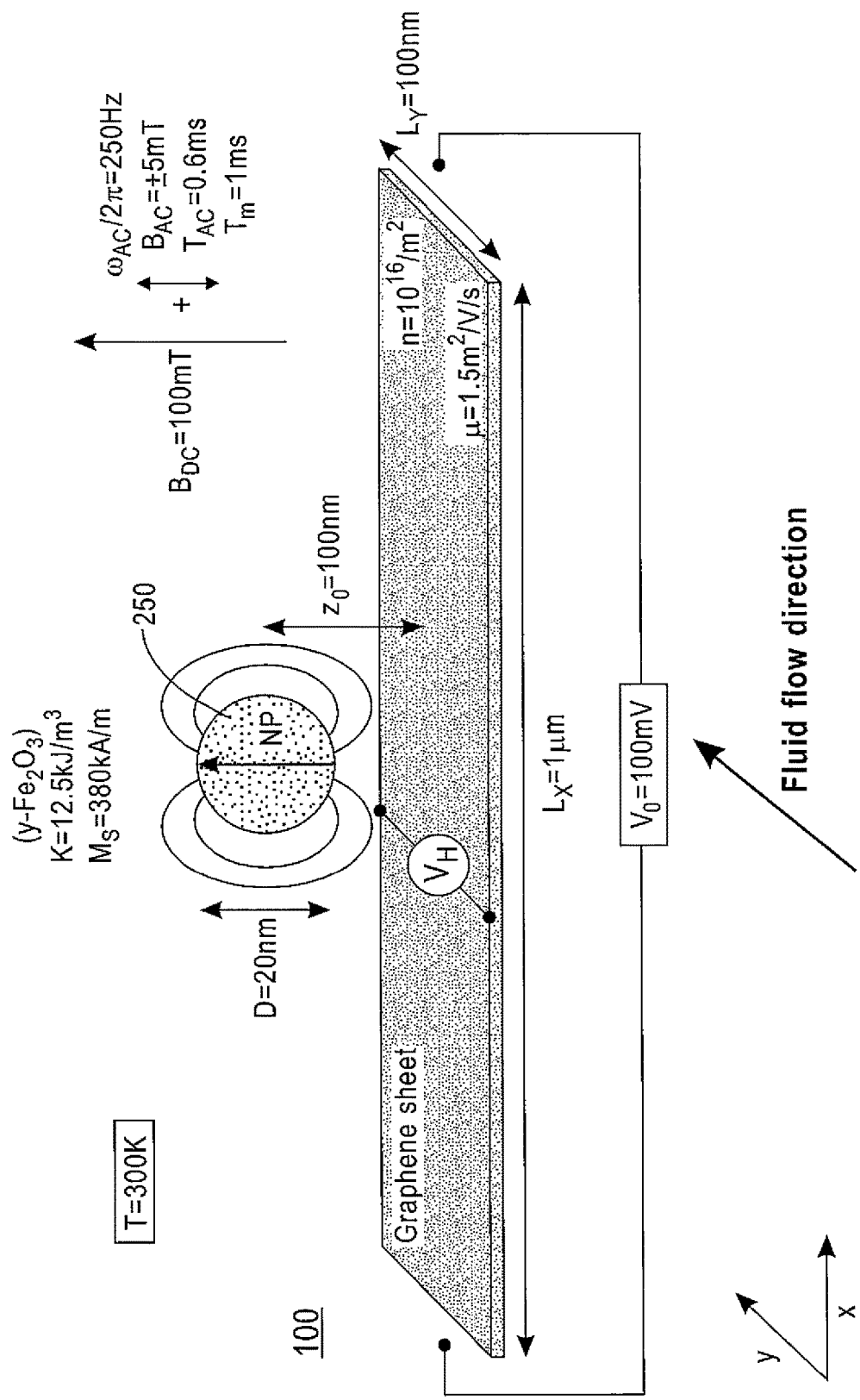
FIG. 16 is a schematic representation of one exemplary principle of operation of the graphene-based Hall effect sensor.

As shown in FIG. 16, one exemplary operation principle for the detection of magnetic nanoparticles using the sensor 100 is shown. In order to improve detectability of a magnetic nanoparticle 250 using the sensor 100, a small AC magnetic field of a few millitesla (mT) operating at a frequency of hundreds of Hertz (Hz) is used to induce an in-phase AC magnetization in the nanoparticle. The induced magnetization of the nanoparticle 250 generates an external AC field at the graphene 130 of the sensor 100. By superimposing an external DC magnetic field on the external AC field, an AC Hall voltage measured across the graphene 130 will be greatly increased by the presence of the nanoparticle 250 as compared to an identical system without a magnetized nanoparticle 250 close to the sensor 100. The AC Hall voltage can be measured using a lock-in amplifier operating at a frequency of the external field. Based on this measured AC Hall voltage, an AC contribution to the magnetic field can be deduced.

In the example embodiment shown, a nanoparticle 250 of $\gamma$-$Fe_2O_3$ of about 20 nm in diameter is detected using a sheet of graphene 130 about 1 μm in width ($L_x$) and about 100 nm in length ($L_y$) and across which a biasing voltage of 100 mV is applied. The nanoparticle 250 has an energy density (K) of 12.5 kilojoules per cubic meter ($kJ/m^3$) and a magnetic field strength ($M_s$) of 380 kiloamperes per meter (kA/m). The graphene 130 has an electron mobility (μ) of 1.5 square meters per volt second ($m^2/(Vs)$) and an assumed charge carrier density (n) in the graphene 130 used for simulations of $10^{16}/m^2$. The AC magnetic field applied is about 5 mT at 250 Hz. Relaxation times with regard to the applied AC ($T_{AC}$) and DC magnetic fields ($T_m$) are 0.6 ms and 1 ms, respectively. The nanoparticle 250 is detectable at a distance of about 100 nm from the graphene 130. Although particular physical values are attributed to the drawing, the operation principle described herein is not limited to those particular values.

Figure 17A:
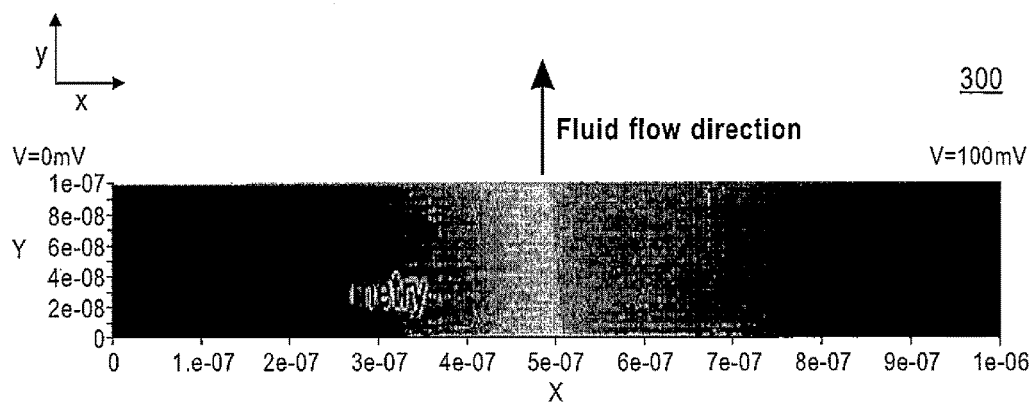
FIGS. 17A-17C are computer simulation results of the operation of sensors employing , various graphene layer geometries.
Figure 17B:
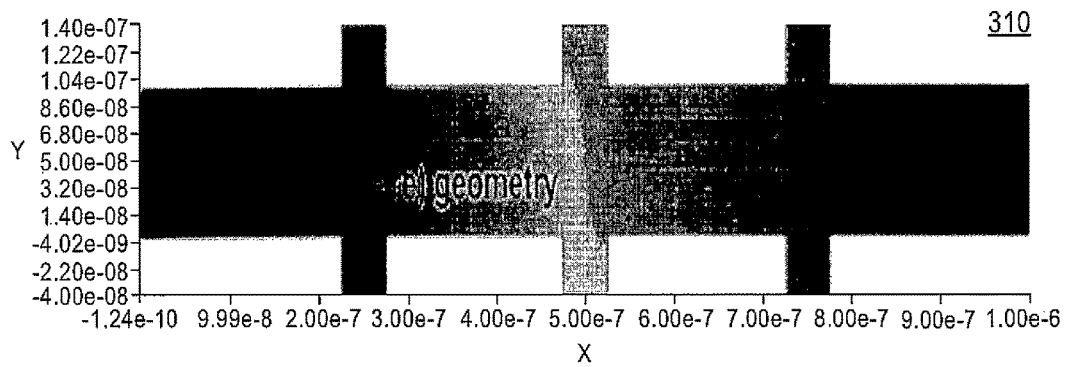
Figure 17C:
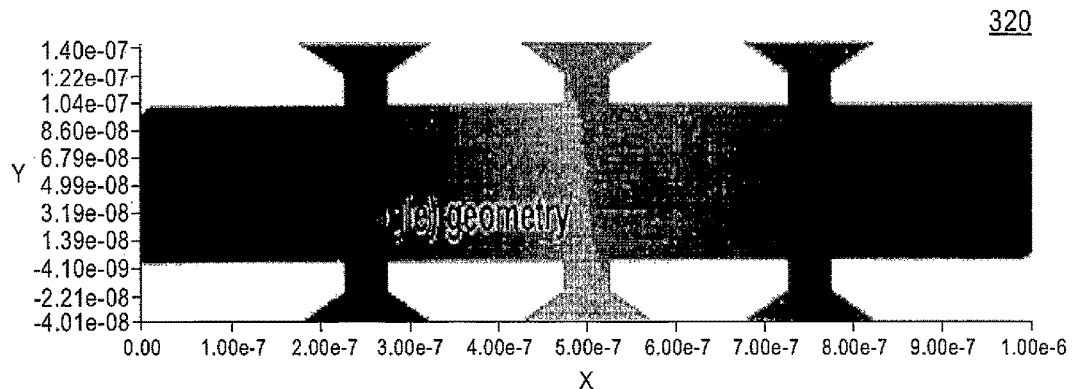

As shown in FIGS. 17A-17C, simulations of the operation of the sensor 100 exemplified in FIG. 16, but employing various graphene layer geometries, are shown generally at 300, 310, and 320. A sensor 100 having the multiple-cross geometry, as indicated at 310 and 320 in FIGS. 17B and 17C, respectively, allows for independent measurements of the Hall voltage at different X positions across a fluid channel. The crosses also facilitate the electrical contact for the voltage measurements. In these simulations, the magnetic nanoparticle 250 was placed at the center of the graphene 130. Measuring the Hall voltage anywhere else other than at the central cross (as well as, for example, anywhere across the sensor 100 as indicated in FIG. 17A) will give zero signal. This feature allows for spatial resolution along X regarding the detection of the nanoparticle 250. The multi-cross geometry may have an arbitrary number (N) of crosses, not just 3 as depicted. For larger numbers of crosses, the detection resolution across the channel will accordingly improve. This detection scheme allows for detecting the presence of magnetic nanoparticles 250, thereby enabling the use of the sensor 100 for biological immunoassays, where a detection antibody may be labeled with a magnetic nanoparticle 250 for determining the presence of an antigen.

Figure 18A:
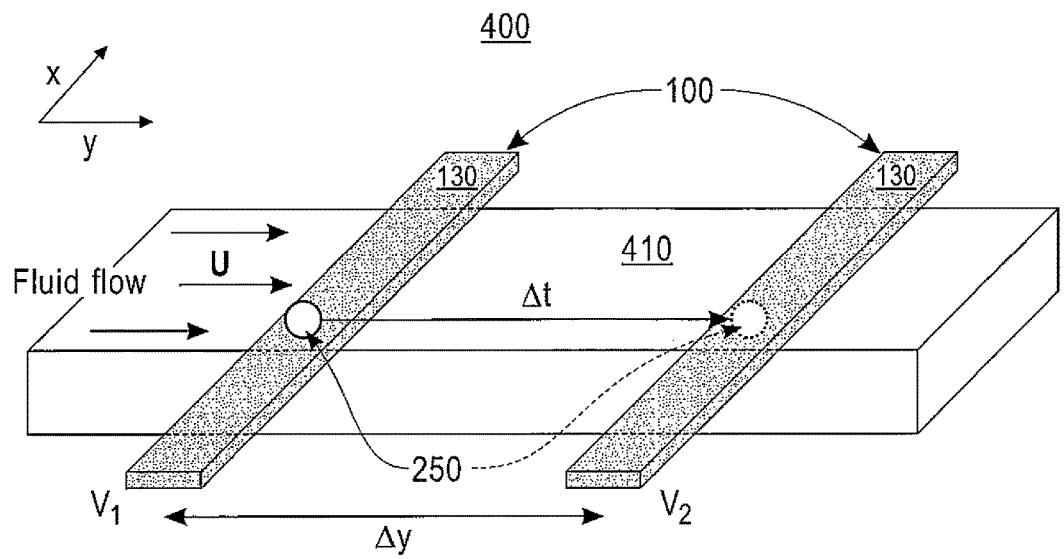
FIG. 18A is a schematic representation of one exemplary determination of 2-dimensional flow -fields using multiple sensors.
Figure 18B:
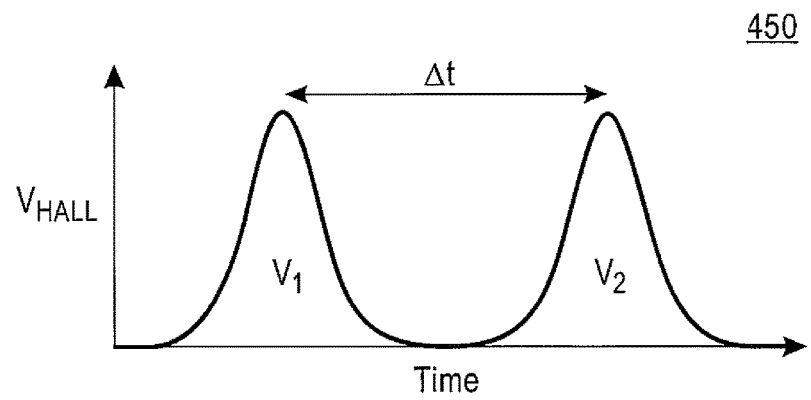
FIG. 18B is a graphical representation of sequential Hall voltage signals determined over time shifts.

As shown in FIGS. 18A and 18B, a determination of 2-dimensional flow velocity fields is shown generally at 400. By placing multiple sensors 100, each comprising a graphene sheet 130, at several positions along the channel (indicated at 410), a series of time-shifted Hall voltage signals can be measured when a magnetic nanoparticle 250 flows along the channel 410. By cross-correlating these multiple Hall voltage signals using the equation:

$$V_{corr}(\Delta t) = \int dt' V_1(t') \cdot V_2(t' + \Delta t) \quad \text{(Eq. 1)}$$

where $V_{corr}$ is the correlated voltage, $V_1$ is a first Hall voltage signal, $V_2$ is a second Hall voltage signal, and t is time, it is possible to determine the time-shift between the voltage signals which, together with the spatial distance between the graphene sheets, gives the average flow speed of the surrounding fluid in that region as indicated by:

$$U = \Delta Y/\Delta t \quad \text{(Eq. 2)}$$

where U is speed, Y is distance along the channel, and t is time. The sequential Hall voltage signals ($V_1$, $V_2$) are determined over time-shifts ($\Delta t$), as indicated graphically at 450 in FIG. 18B. Thus, it is illustrated how the average flow speed of the fluid could be'determined by employing two sensors 100 displaced a known distance ($\Delta Y$) along the channel 410 (which may be a nanochannel or a microchannel). This velocimetry technique may use an arbitrary number (M) of sensors 100, not just two as depicted. Such array of M equally spaced sensors 100 may improve the signal-to-noise ratio of the cross-correlation calculation involved in the determination of the time-shifts ($\Delta t$).

Since the magnetic field of a nanoparticle 250 is very localized, by measuring the Hall voltage at different locations of the graphene 130, the position of the nanoparticle 250 with X (wall-normal) and Y (streamwise) resolution can be determined, providing two-dimensional information on the presence of nanoparticles 250. By allying this two-dimensional positional information with the cross-correlation of the time-shifted signals received from different positions along the channel 410, a two-dimensional flow velocity field of the surrounding fluid can be obtained using only the magnetic character of the tracers.

Figure 19:
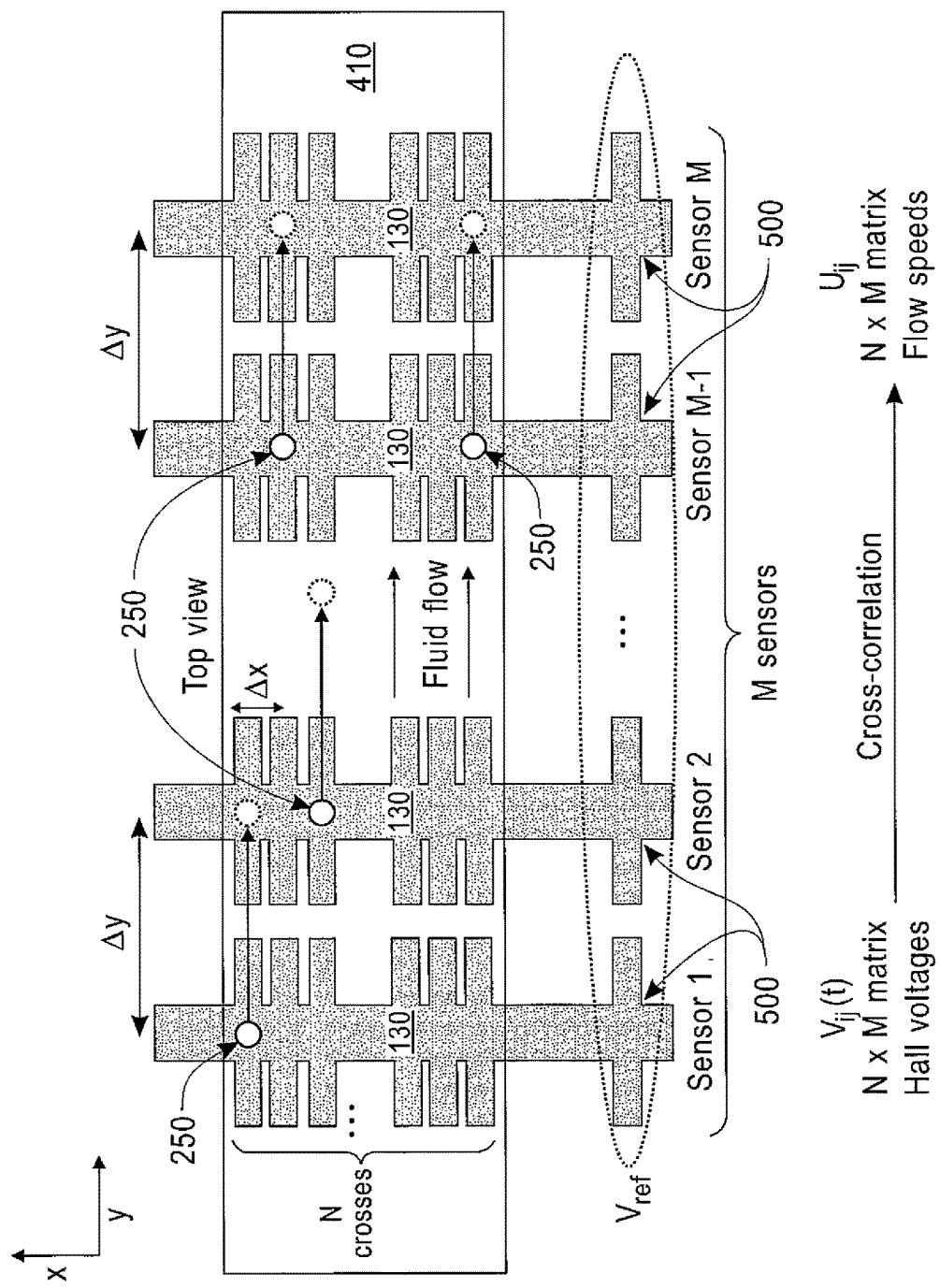
FIG. 19 is a schematic representation of one exemplary illustration of a determination of a velocity field.

FIG. 19 illustrates how a velocity field determination could be obtained using a matrix of N crosses by M sensors with resolution $\Delta X$ and $\Delta Y$ in the wall-normal and streamwise directions of the channel 410, respectively. An additional cross (shown at 500, located external to the flow of magnetic particles 250 in the channel 410), could be included for providing a reference signal $V_{ref}$ and further improving the reliability of the detection scheme.

Additionally, a determination of 3-dimensional flow velocity fields could also be made. For example, with a knowledge of the properties (size and material) of the magnetic nanoparticles 250, a vertical position of a nanoparticle 250 can be inferred by exploring the reciprocal of the distance-cubed of the magnetic field at large distances. Since the Hall voltage depends on the strength of the magnetic field associated with the nanoparticle 250, the Hall signal will be modulated by the vertical distance between the nanoparticle 250 and the graphene 130, offering an additional source of information that could potentially enable 3-dimensional localization of nanoparticles 250. By allying the 3-dimensional positional information pertaining to the nanoparticles 250 with the cross- correlation of time- shifted signals coming from an array of sensors 100 at different positions along the channel 410, a 3-dimensional flow velocity field of the surrounding fluid may be obtained.

Figure 20:
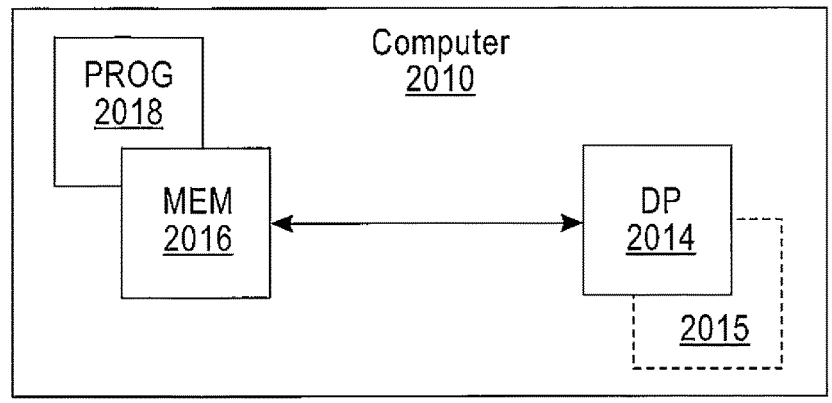
FIG. 20 is a block diagram of various electronic devices and apparatuses that may be suitable for use in providing a fluid flow analysis.

Referring now to FIG. 20, a simplified block diagram of various electronic devices and apparatuses that are suitable for use in practicing the exemplary embodiments described herein is shown. For example, a computer 2010 may be used to control one or more of the processes as described above. The computer 2010 includes a controller, such as a computer or a data processor (DP) 2014 and a computer-readable memory medium embodied as a memory (MEM) 2016 that stores a program of computer instructions (PROG) 2018.

The PROG 2018 includes program instructions that, when executed by the associated DP 2014, enable the various electronic devices and apparatuses to operate in accordance with exemplary embodiments. That is, various exemplary embodiments may be implemented at least in part by computer software executable by the DP 2014 of the computer 2010, or by hardware, or by a combination of software and hardware (and firmware).

The computer 2010 may also include dedicated processors, for example a processor 2015 that controls the inducement of in-phase AC magnetization in the nanoparticle 250, measures a generated AC contribution to the magnetic field at the sensor 100, superimposes an external DC magnetic field on an external AC field, and/or measures an AC Hall voltage across a graphene portion of the-sensor 100.

The computer readable MEM 2016 may be of any type suitable to the local technical environment and may be implemented using any suitable data storage technology, such as semiconductor based memory devices, flash memory, magnetic memory devices and systems, optical memory devices and systems, fixed memory, and removable memory. The DP 2014 may be of any type suitable to the local technical environment, and may include one or more of general purpose computers, special purpose computers, microprocessors, digital signal processors (DSPs), and processors based on a multicore processor architecture, as non-limiting examples.

The exemplary embodiments, as discussed herein and as particularly described with respect to exemplary methods, may be implemented in conjunction with a program storage device (e.g., at least one memory) readable by a machine, tangibly embodying a program of instructions (e.g., a program or computer program) executable by the machine for performing operations. The operations comprise utilizing the exemplary embodiments of the methods described herein.

Based on the foregoing, it should be apparent that various exemplary embodiments. provide methods for the detection and characterization of magnetic nanoparticles while dispersed in a carrying fluid flowing through a channel.

Figure 21:
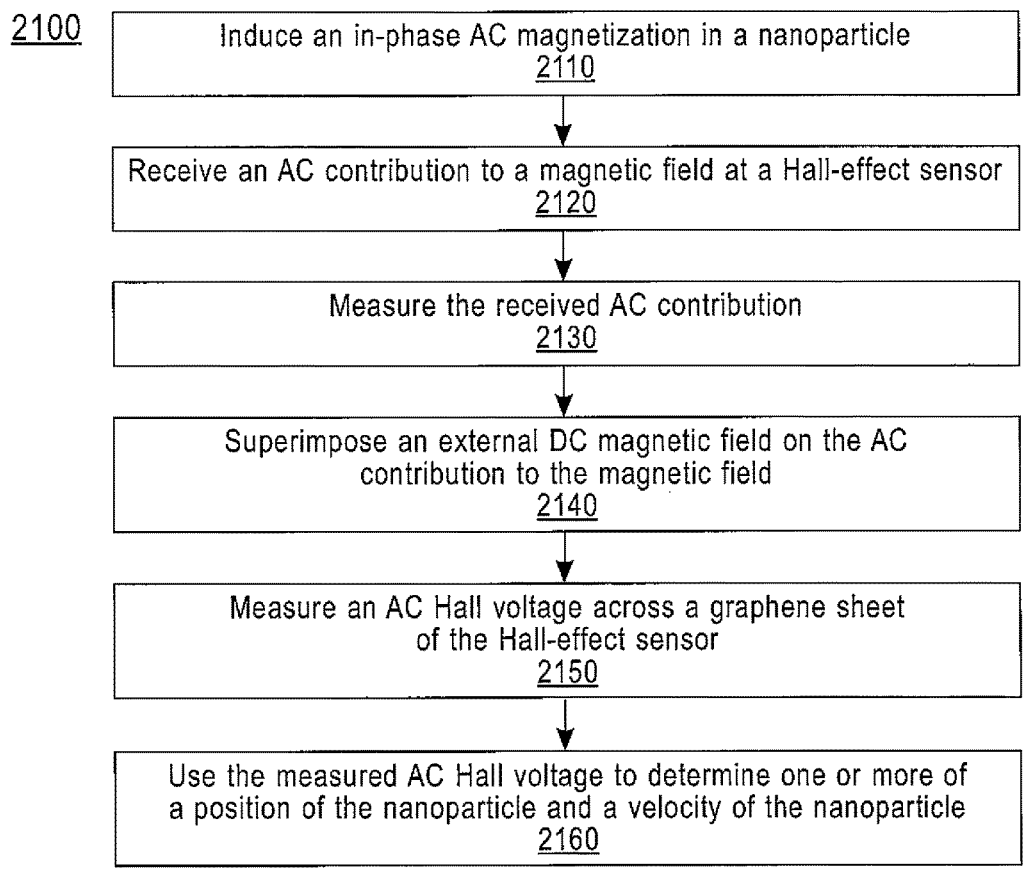
FIG. 21 is a logic flow diagram that illustrates the operation of one exemplary method, and a result of execution of computer program instructions embodied on a computer readable memory, in accordance with an exemplary embodiment of providing a fluid flow analysis.

FIG. 21 is a logic flow diagram that illustrates the operation of one exemplary embodiment of a method 2100 for the detection and characterization of magnetic nanoparticles while dispersed in a carrying fluid flowing through a channel. In method 2100, at 2110, an in-phase AC magnetization is induced in a nanoparticle. At 2120, an AC contribution to a magnetic field is received at a Hall-effect sensor. The received AC contribution is measured at 2130, and an external DC magnetic field is superimposed on the AC contribution to the magnetic field at 2140. At 2150, an AC Hall voltage is measured across a graphene sheet of the Hall-effect sensor. At 2160, the measured AC Hall voltage is used to determine one or more of a position of the nanoparticle and a velocity of the nanoparticle in a fluid.

In one exemplary aspect, a method of detecting a particle comprises magnetizing a particle using an AC magnetic field; generating an AC voltage, from the magnetized particle, in a sensing device having a conductive substantially 2-dimensional lattice structure; superimposing a DC magnetic field on the generated AC voltage in the sensing device; and measuring an AC Hall voltage at the sensing device.

In the method, generating an AC voltage, from the magnetized particle, in a sensing device may comprise applying an AC voltage across an AC coil on the sensing device. Superimposing a DC magnetic field on the generated AC voltage in the sensing device may increase the AC Hall voltage for measuring at the sensing device as compared to a generated AC voltage in the sensing device without a DC magnetic field superimposed thereon. Superimposing a DC magnetic field on the generated AC voltage in the sensing device may comprise applying a DC voltage across a DC coil on the sensing device. The method may further comprise applying a source voltage across opposing ends of the conductive substantially 2-dimensional lattice structure. Generating an AC voltage in a sensing device having a conductive substantially 2-dimensional lattice structure from the magnetized particle may comprise generating an AC voltage in a graphene element biased with a voltage.

In another exemplary aspect, a method of determining a flow velocity field comprises magnetizing a particle in a fluid flowing in a channel by applying an AC magnetic field to the particle; measuring a first AC Hall voltage at a first sensing device in the channel, the first sensing device comprising a first graphene element biased with a voltage; measuring a second AC Hall voltage at a second sensing device in the channel, the second sensing device comprising a second graphene element biased with a voltage; determining a time-shift between the first measured AC Hall voltage and the second measured AC Hall voltage; and determining a fluid flow velocity in the channel based on the determined time-shift and a spatial distance between the first sensing device and the second sensing device.

Measuring a first AC Hall voltage at a first sensing device in the channel may comprise generating an AC voltage, from the magnetized particle, in a conductive substantially 2-dimensional lattice structure of the first sensing device, and superimposing a DC magnetic field on the generated AC voltage in the conductive substantially 2-dimensional lattice structure of the first sensing device. Determining a time-shift between the first measured AC Hall voltage and the second measured AC Hall voltage may comprise cross-correlating the first measured AC Hall voltage and the second measured AC Hall voltage using Equation (1) as described herein. An average flow speed of the fluid flowing in the channel may be indicated by Equation (2) as described herein. The method may further comprise providing a reference voltage to the first sensing device and the second sensing device external to the channel.

In another exemplary aspect, an apparatus comprises a first coil for providing a DC magnetic field; a second coil for providing an AC magnetic field; and a conductive substantially 2-dimensional lattice structure proximate the first coil and the second coil and being biased with a voltage. The first coil, the second coil, and the conductive substantially 2-dimensional lattice structure are separated by dielectric layers.

The apparatus may further comprise a first set of contacts disposed in contact with the conductive substantially 2-dimensional lattice structure. The apparatus may further comprise a first set of vias in contact with the first coil and a second set of vias in contact with the second coil. The conductive substantially 2-dimensional lattice structure may comprise graphene. The conductive substantially 2-dimensional lattice structure may comprise $MoS_2$, $WSe_2$, black phosphorous, carbon nanotubes, Si nanowire, or a combination of any of the foregoing materials. At least one of the dielectric layers may be disposed on a substrate of glass, quartz, SiC, silicon nitride, plastic, or a combination of any of the foregoing materials. At least one of the dielectric layers may comprise $SiO_2$, $Al_2O_3$, HfO, or a combination of any of the foregoing materials. The second coil may be a thin linear element.

The foregoing description has provided by way of exemplary and non-limiting examples a full and informative description of the best method and apparatus presently contemplated by the inventors for carrying out various exemplary embodiments. However, various modifications and adaptations may become apparent to those skilled in the relevant arts in view of the foregoing description, when read in conjunction with the accompanying drawings and the appended claims. However, all such and similar modifications will still fall within the scope of the teachings of the exemplary embodiments.

Furthermore, some of the features of the preferred embodiments could be used to advantage without the corresponding use of other features. As such, the foregoing description should be considered as merely illustrative of the principles, and not in limitation thereof.

What is claimed is:

1. A method of determining a flow velocity field, comprising:
    magnetizing a particle in a fluid flowing in a channel by applying an AC magnetic field to the particle;
    measuring a first AC Hall voltage at a first sensing device in the channel, the first sensing device comprising a first graphene element biased with a voltage;
    measuring a second AC Hall voltage at a second sensing device in the channel, the second sensing device comprising a second graphene element biased with a voltage;
    determining a time-shift between the first measured AC Hall voltage and the second measured AC Hall voltage; and
    determining a fluid flow velocity in the channel based on the determined time-shift and a spatial distance between the first sensing device and the second sensing device.

2. The method of claim 1, wherein measuring a first AC Hall voltage at a first sensing device in the channel comprises,
    generating an AC voltage, from the magnetized particle, in a conductive substantially 2-dimensional lattice structure of the first sensing device, and
    superimposing a DC magnetic field on the generated AC voltage in the conductive substantially 2-dimensional lattice structure of the first sensing device.

3. The method of claim 1, wherein determining a time-shift between the first measured AC Hall voltage and the second measured AC Hall voltage comprises cross-correlating the first measured AC Hall voltage and the second measured AC Hall voltage using the equation:

$$V_{corr}(\Delta t) = \int dt' V_1(t') \cdot V_2(t' + \Delta t)$$

where $V_{corr}$ is the correlated voltage, $V_1$ is a first Hall voltage signal, $V_2$ is a second Hall voltage signal, and t is time.

4. The method of claim 3, wherein an average flow speed of the fluid flowing in the channel is indicated by:

$$U \Delta Y / \Delta t$$

where U is speed, Y is distance along the channel, and t is time.

5. The method of claim 1, further comprising providing a reference voltage to the first sensing device and the second sensing device external to the channel.

6. The method of claim 1, further comprising measuring a third AC Hall voltage at a third sensing device in the channel, the third sensing device comprising a third graphene element biased with a voltage and being arranged with the first sensing device and the second sensing device to form an array of equally spaced sensors.

7. The method of claim 1, further comprising determining two-dimensional information related to the particle, the two-dimensional information being determined based on measuring the first AC Hall voltage, measuring the second AC Hall voltage, and measuring a third AC Hall voltage to determine a position of the particle with X and Y resolution.

8. The method of claim 7, further comprising allying the determined two-dimensional information related to the particle with at least two time-shifted signals from at least two different positions along the channel.

9. The method of claim 1, further comprising determining three-dimensional information related to the particle, the three-dimensional information being determined based on an inferred vertical position of the particle.

10. The method of claim 9, wherein the inferred vertical position of the particle is based on a strength of a Hall voltage modulated by a vertical distance between the particle and at least one of the first graphene element and the second graphene element.

11. A method of determining a velocity field, the method comprising:
providing a matrix of cross-shaped graphene sensors in a fluid flow path;
magnetizing a particle in the fluid flow path by applying an AC magnetic field to the particle;
measuring a first AC Hall voltage at a first cross-shaped graphene sensor in the matrix of cross-shaped graphene sensors;
measuring a second AC Hall voltage at a second cross-shaped graphene sensor in the matrix of cross-shaped graphene sensors;
determining a fluid flow velocity in the fluid flow path based on a change in position of the particle in a direction across the fluid flow path and in a streamwise direction with the fluid flow path.

12. The method of claim 11, wherein determining a fluid flow velocity comprises measuring a time-shift between the first measured AC Hall voltage and the second measured AC Hall voltage.

13. The method of claim 12, wherein measuring a time-shift between the first measured AC Hall voltage and the second measured AC Hall voltage comprises cross-correlating the first measured AC Hall voltage and the second measured AC Hall voltage using the equation:

$$V_{corr}(\Delta t) = \int dt' V_1(t') \cdot V_2(t'+\Delta t)$$

where $V_{corr}$ is the correlated voltage, $V_1$ is a first Hall voltage signal, $V_2$ is a second Hall voltage signal, and t is time.

14. The method of claim 11, further comprising locating a portion of each cross-shaped graphene sensor of the matrix of cross-shaped graphene sensors external to the flow of the particle in the fluid flow path.

15. The method of claim 14, further comprising providing a reference voltage signal to each externally-located portion.

16. The method of claim 11, further comprising inferring a vertical position of the particle to determine three-dimensional information related to the particle.

17. The method of claim 16, wherein the inferred vertical position of the particle is based on a strength of a Hall voltage modulated by a vertical distance between the particle and at least one of the first cross-shaped graphene sensor in the matrix of cross-shaped graphene sensors and the second cross-shaped graphene sensor in the matrix of cross-shaped graphene sensors.

* * * * *